United States Patent
Kuo et al.

(10) Patent No.: US 6,897,316 B2
(45) Date of Patent: May 24, 2005

(54) SUBSTITUTED 2-PHENYL-4-QUINOLONE-3-CARBOXYLIC ACID COMPOUNDS AND THEIR USE AS ANTITUMOR AGENTS

(75) Inventors: Sheng-Chu Kuo, Taichung (TW); Li-Jiau Huang, Taichung (TW); Ya-Yun Lai, Taichung (TW); Chun-Jen Chen, Taichung (TW); Mei-Hua Hsu, Taichung (TW); Ya-Ling Fang, Taichung (TW); Kuo-Hsiung Lee, Chapel Hill, NC (US); Che-Ming Teng, Taipei (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 10/636,603

(22) Filed: Aug. 8, 2003

(65) Prior Publication Data

US 2005/0032832 A1 Feb. 10, 2005

(51) Int. Cl.[7] ................... C07D 215/16; C07D 215/20; A61K 31/47

(52) U.S. Cl. ................... 546/157; 546/158; 514/312; 514/314

(58) Field of Search ................... 546/157, 158; 514/312, 314

(56) References Cited

PUBLICATIONS

Rao, abstract CA 137:294853, abstract of J of Chem Society, Perkin Trans 1, vol. 10, pp 1232–1235, 2002.*

Hall, 'Quinoline Derivatives as Antiallergy Agents', J of Med Chem, vol. 17(7), pp 685–690, 1974.*

Jung, 'Synthesis and Antibacterial Activity . . . ', Farmaco, VOl 56(9), pp665–675, 2001.*

* cited by examiner

Primary Examiner—D. Margaret Seaman
(74) Attorney, Agent, or Firm—Bacon & Thomas

(57) ABSTRACT

Substituted 2-phenyl-4-quinolone-3-carboxylic acid derivatives and their salts were synthesized. The results of preliminary screening revealed that these compounds are potent in killing solid tumor cancers.

13 Claims, No Drawings

SUBSTITUTED 2-PHENYL-4-QUINOLONE-3-CARBOXYLIC ACID COMPOUNDS AND THEIR USE AS ANTITUMOR AGENTS

FIELD OF THE INVENTION

The present invention relates to a series of substituted 2-phenyl-4-quinolone-3-carboxylic acid compounds; and in particular to their uses in treating human cancers.

BACKGROUND OF THE INVENTION

Quinolone derivatives were initially discovered as the agents to act on bacterial DNA gyrase, and thus developed as anti-bacterial agents. Recently DNA topoisomerase II has emerged as the pharmacological target for this class of quinolone compounds. We have synthesized a series of substituted 2-phenyl-4-quinolone (A) which appeared to function as novel antimitotic agents. [Kuo, S. C., Lee, H. Z., Juang, J. P., Lin, Y. T., Wu, T. S., Chang, J. J., Lednicer, D., Paull, K. D., Lin, C. M., Hamel, E. Synthesis and cytotoxicity of 1,6,7,8-substituted 2-(4'-substituted phenyl)-4-quinolones and related compounds: identification as antimitotic agents interacting with tubulin. *J. Med. Chem.* 1993, 36, 1146–56; Li, L., Wang, H. K., Kuo, S. C., Wu, T. S., Mauger, A., Lin. C. M., Hamel, E. Lee, K. H. Antitumor agents. 155. Synthesis and biological evaluation of 3',6,7-substituted 2-phenyl-4-quinolones as antimicrotubule agents. *J. Med. Chem.* 1994, 37, 3400–7] Later on we continued to synthesize many related analogs such as 2-phenylnaphthyridine-4-ones (B) [Chen, K., Kuo, S. C., Hsieh, M. C., Mauger, S A., Lin, C. M., Hamel, E., Lee, K. H. Antitumor agents. 174. 2',3',4',5,6,7-Substituted 2-phenyl-1,8-naphthyridin-4-ones: their synthesis, cytotoxicity, and inhibition of tubulin polymerization. *J. Med. Chem.* 1997, 40, 2266–75], 2-phenyl-4-quinazolones (C) [Xia, Y., Yang, Z. Y., Hour, M. J., Kuo, S. C., Xia, P., Bastow, K. F., Nakanishi, Y., Namrpoothiri, P., Hackl, T., Hamel, E., Lee, K. H. Antitumor Agents. Part 204: Synthesis and Biological Evaluation of Substituted 2-Aryl Quinazolinones, *Bioorg. Med. Chem. Lett.* 2001, 11, 1193–6; Hour, M. J., Huang, L. J., Kuo, S. C., Xia, Y., Bastow, K. F., Nakanishi, Y., Hamel, E., Lee, K. H. 6-Alkylamino- and 2,3-dihydro-3'-methoxy-2-phenyl-4-quinazolinones and related compounds: their synthesis, cytotoxicity, and inhibition of tubulin polymerization. *J. Med. Chem.* 2000, 43, 4479–87] and tetrahydro-2-phenyl-4-quinolones (D) [Xia, Y., Yang, Z. Y., Xia, P., Bastow, K. F., Tachibana, Y., Kuo, S. C., Hamel, E., Hackl. T., Lee, K. H. Antitumor agents. 181. Synthesis and biological evaluation of 6,7,2',3',4'-substituted-1,2,3,4-tetrahydro-2-phenyl-4-quinolones as a new class of antimitotic antitumor agents. *J. Med. Chem.* 1998, 41. 1155–62], which enable us to establish structure and activity relationships (SAR). Among these analogs, we have discovered quite a few compounds possessing potent cytotoxicity, such as 3',6-disubstitued 2-phenyl-4-quinolones (A-1) etc [Li, L., Wang, H. K., Kuo, S. C., Wu, T. S., Lednicer, D., Lin, C. M., Hamel, E., Lee, K. H. Antitumor agents. 150. 2',3',4',5',5,6,7-substituted 2-phenyl-4-quinolones and related compounds: their synthesis, cytotoxicity, and inhibition of tubulin polymerization. *J. Med. Chem.* 1994, 37, 1126–35]. However, most of the compounds with potent cytotoxicity were very lipophilic, and therefore, not suitable for in vivo and clinical studies. We thus made attempt to introduce carboxylic acid group on the 2-phenyl-4-quinolone skelecton in order to improve pharmacokinetic properties suitable for in vivo and clinical studies.

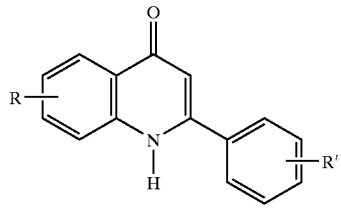

(A)

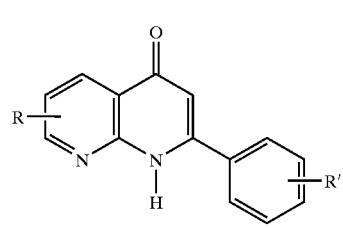

(B)

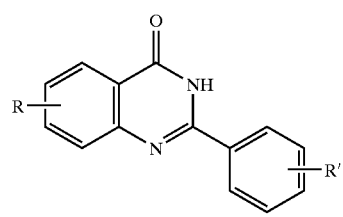

(C)

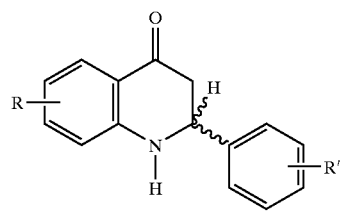

(D)

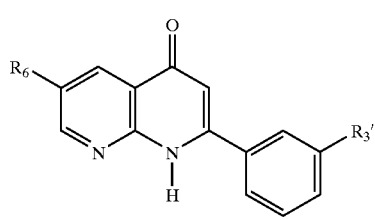

(A-1)

$R_6, R_3' = F, Cl, OCH_3$

SUMMARY OF THE INVENTION

The present invention synthesizes a substituted 2-phenyl-4-quinolone-3-carboxylic acid compound having the formula (I) and its salt:

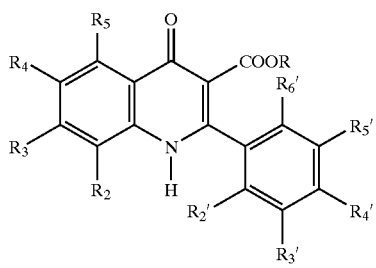

(I)

wherein $R_2'$, $R_3'$, $R_4'$, $R_5'$ and $R_6'$ independently are H, $(CH_2)_nCH_3$, $(CH_2)_nYH$, $Y(CH_2)_nCH_3$, $Y(CH_2)_nYH$, $Y(CH_2)_nNR_8R_9$, X, or $NR_8R_9$, wherein n is an integer of 0~4, Y is O or S, X is F, Cl, or Br, and $R_8$ and $R_9$ independently are H, $(CH_2)_nYH$, $(CH_2)_nN(C_nH_{2n+1})$ or $(CH_2)_nCH_3$, wherein n and Y are defined as above, and m is an integer of 0~4;

$R_2$, $R_3$, $R_4$ and $R_5$ independently are H, $(CH_2)_nCH_3$, $(CH_2)_nYH$, $Y(CH_2)_nCH_3$, $Y(CH_2)_nYH$, $Y(CH_2)_nNR_8R_9$, X, $NR_8R_9$,

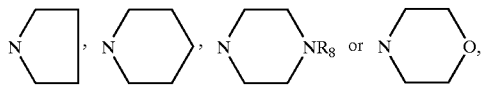

or $R_3$ and $R_4$ together is $—Y(CH_2)_nY—$, wherein n, Y, X, $R_8$ and $R_9$ are defined as above, preferably $R_3$ and $R_4$ together is $—OCH_2O—$; and R is H.

Preferably, $R_2'$, $R_4'$, $R_5'$ and $R_6'$ are H; and $R_3'$ is H, $Y(CH_2)_nCH_3$, $NH(CH_2)_nCH_3$ or X, wherein n, Y and X are defined as above; $R_3$ is H; and $R_4$ is $Y(CH_2)_nCH_3$, or X, wherein n and X are defined as above. More preferably, $R_3'$ and $R_4$ independently are methoxy, F or Cl. Most preferably, $R_3'$ is F and $R_4$ is methoxy.

Preferalby, the salt of the compound (I) is a quaternary ammonium salt or pharmaceutically acceptable inorganic salt.

The present invention also discloses a pharmaceutical composition for the killing of solid tumor cells, which comprises a therapeutically effective amount of a substituted 2-phenyl-4-quinolone-3-carboxylic acid compound of the formula (I) as set forth in any one of claim 1 to claim 4 or a pharmaceutically acceptable salt thereof, as an active ingredient, in admixture with a pharmaceutically acceptable carrier or diluent for the active ingredient, wherein the solid tumor cells comprise human breast cancer, CNS cancer, colon cancer, lung cancer, melanoma, ovarian cancer, renal cancer, stomach cancer, prostate cancer, ileocecal carcinoma, glioblastoma, bone cancer, or epidermoid carcinoma of the nasopharynx.

The present invention further discloses a method of killing solid tumor cancers comprising administering a therapeutically effective amount of a substituted 2-phenyl-4-quinolone-3-carboxylic acid compound of the formula (I) as set forth in any one of claim 1 to claim 8 to a subject having solid tumor cells, wherein the solid tumor cells comprise human breast cancer, CNS cancer, colon cancer, lung cancer, melanoma, ovarian cancer, renal cancer, stomach cancer, prostate cancer, ileocecal carcinoma, glioblastoma, bone cancer, or epidermoid carcinoma of the nasopharynx.

DETAILED DESCRIPTION OF THE INVENTION

The synthesis of key intermediates, 3-ethoxy carbonyl derivatives of substituted 2-phenyl-4-quinolones (VII) was illustrated in the following Schemes 1 and 2. At first, the reaction of substituted anilines (I) with substituted benzyl chlorides (II) in toluene, at room temperature, yielded the corresponding N-(substituted phenyl)-substituted benzamides (III), subsequent chlorination of compounds III with $PCl_5$ afforded the carboximidoyl chlorides (IV) that, without further purification, where then treated with sodium diethylmalonate in toluene to give their corresponding N-[1-(substituted phenyl)-2-diethoxycarbonylvinyl]-N-(4-substituted phenyl)amines (V).

In the next step, these intermediates V were used without purification and were thermally cyclized into their corresponding ethyl substituted 2-phenyl-4-quinolone-3-carboxylates (VII). At the same time, substituted 2-phenyl-4-quinolones (VIII-1~4) were obtained, during the purification of products VII-1~3 and VII-6, as their de-ethoxycarboxylate derivatives. This indicated that mono-ethoxycarbonyl vinyl derivatives (VI) might have also been produced in side reaction during the preparation of intermediates V-1~3 and V-6. Indeed, the mono-ethoxycarbonyl vinyl derivative (VI-1) was isolated. Thermal cyclization of the mono-ethoxycarbonyl vinyl intermediates (VI-1) also led to the formation of 3'-chloro-6-fluoro-2-phenyl-4-quinolone (VIII-1).

The synthetic routes from key intermediates VII to the target compounds IX, X were illustrated in the following Scheme 3. As shown, compounds VII were first hydrolyzed into carboxylic acids (IX) which were subsequently treated with tromethamine in mixed butyl chloride/methanol solvent to afford the corresponding salts (X).

Scheme 1

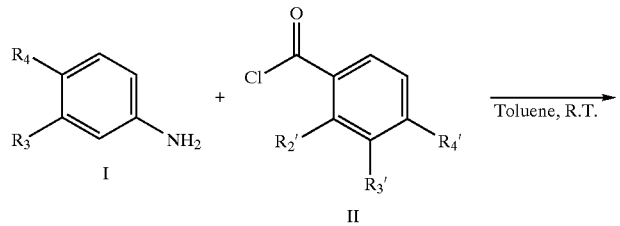

I
1. $R_4 = F, R_3 = H$
2. $R_4 = Cl, R_3 = H$
3. $R_4 = OCH_3, = H$
4. $R_4 = R_3 = H$
5. $R_3, R_4 = $ ——$OCH_2O$——

II
1. $R_3' = Cl, R_2' = R_4' = H$
2. $R_3' = F, R_2' = R_4' = H$
3. $R_3' = OCH_3, R_2' = R_4' = H$
4. $R_2' = R_3' = R_4' = H$
5. $R_2' = Cl, R_3' = R_4' = H$
6. $R_2' = F, R_3' = R_4' = H$
7. $R_2' = OCH_3, R_3' = R_4' = H$
8. $R_4' = F, R_2' = R_3' = H$

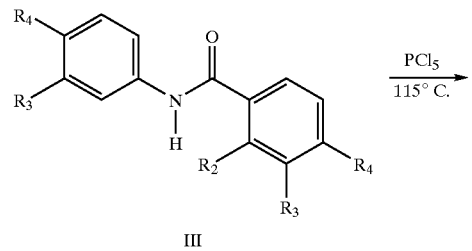

III
1. $R_4 = F, R_3' = Cl, R_3 = R_2' = R_4' = H$
2. $R_4 = R_3' = F, R_3 = R_2' = R_4' = H$
3. $R_4 = F, R_3' = OCH_3, R_3 = R_2' = R_4' = H$
4. $R_4 = F, R_3 = R_2' = R_3' = R_4' = H$
5. $R_4 = Cl, R_3' = F, R_3 = R_2' = R_4' = H$
6. $R_4 = R_3' = Cl, R_3 = R_2' = R_4' = H$
7. $R_4 = Cl, R_3' = OCH_3, R_3 = R_2' = R_4' = H$
8. $R_4 = OCH_3, R_3' = F, R_3 = R_2' = R_4' = H$
9. $R_4 = OCH_3, R_3' = Cl, R_3 = R_2 = R_4' = H$
10. $R_4 = R_3' = OCH_3, R_3 = R_2' = R_4' = H$
11. $R_4 = OCH_3, R_3 = R_2' = R_3' = R_4' = H$
12. $R_4 = R_3 = R_2' = R_3' = R_4' = H$
13. $R_4 = Cl, R_2' = F, R_3 = R_3' = R_4' = H$
14. $R_4 = R_2' = Cl, R_3 = R_3' = R_4' = H$
15. $R_4 = Cl, R_2' = OCH_3, R_3 = R_3' = R_4' = H$
16. $R_4 = Cl, R_3 = R_2' = R_3' = R_4' = H$
17. $R_4 = R_2' = F, R_3 = R_3' = R_4' = H$
18. $R_4 = F, R_2' = Cl, R_3 = R_3' = R_4' = H$
19. $R_4 = F, R_2' = OCH_3, = R_3 = R_3' = R_4' = H$
20. $R_4 = OCH_3, R_2' = F, R_3 = R_3' = R_4' = H$
21. $R_4 = OCH_3, R_2' = Cl, R_3 = R_3' = R_4' = H$
22. $R_4 = R_2' = OCH_3, R_3 = R_3' = R_4' = H$
23. $R_4 = OCH_3, R_4' = F, R_3 = R_2' = R_3' = H$
24. $R_2' = Cl, R_3 = R_4 = R_2' = R_4' = H$
25. $R_3, R_4 = $-$OCH_2O$-, $R_2' = R_3' = R_4' = H$

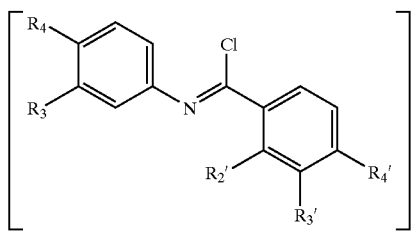

IV
1. $R_4 = F, R_3' = Cl, R_3 = R_2' = R_4' = H$
2. $R_4 = R_3' = F, R_3 = R_2' = R_4' = H$
3. $R_4 = F, R_3' = OCH_3, R_3 = R_2' = R_4' = H$
4. $R_4 = F, R_3 = R_2' = R_3' = R_4' = H$
5. $R_4 = Cl, R_3' = F, R_3 = R_2' = R_4' = H$
6. $R_4 = R_3' = Cl, R_3 = R_2' = R_4' = H$
7. $R_4 = Cl, R_3' = OCH_3, R_3 = R_2' = R_4' = H$
8. $R_4 = OCH_3, R_3' = F, R_3 = R_2' = R_4' = H$
9. $R_4 = OCH_3, R_3' = Cl, R_3 = R_2' = R_4' = H$
10. $R_4 = R_3' = OCH_3, R_3 = R_2' = R_2' = H$
11. $R_4 = OCH_3, R_3 = R_2' = R_3' = R_4' = H$
12. $R_4 = R_3 = R_2' = R_3' = R_4' = H$
13. $R_4 = Cl, R_2' = F, R_3 = R_3' = R_4' = H$
14. $R_4 = R_2' = Cl, R_3 = R_3' = R_4' = H$
15. $R_4 = Cl, R_2' = OCH_3, R_3 = R_3' = R_4' = H$
16. $R_4 = Cl, R_3 = R_2' = R_3' = R_4' = H$
17. $R_4 = R_2' = F, R_3 = R_3' = R_4' = H$
18. $R_4 = F, R_2' = Cl, R_3 = R_3' = R_4' = H$
19. $R_4 = F, R_2' = OCH_3, R_3 = R_3' = R_4' = H$
20. $R_4 = OCH_3, R_2' = F, R_3 = R_3' = R_4' = H$
21. $R_4 = OCH_3, R_2' = Cl, R_3 = R_3' = R_4' = H$
22. $R_4 = OCH_3, R_4' = F, R_3 = R_2' = R_4' = H$
23. $R_3, R_4 = $——$OCH_3$——, $R_2' = R_3' = R_4' = H$

Scheme 2

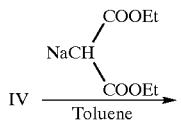

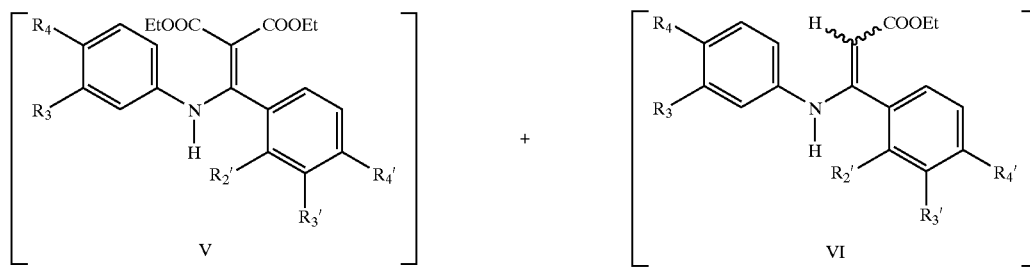

V

1. $R_4 = F, R_3' = Cl, R_3 = R_2' = R_4' = H$
2. $R_4 = R_3' = F, R_3 = R_2' = R_4' = H$
3. $R_4 = F, R_3' = OCH_3, R_3 = R_2' = R_4' = H$
4. $R_4 = F, R_3 = R_2' = R_3' = R_4' = H$
5. $R_4 = Cl, R_3' = F, R_3 = R_2' = R_4' = H$
6. $R_4 = R_3' = Cl, R_3 = R_2' = R_4' = H$
7. $R_4 = Cl, R_3' = OCH_3, R_3 = R_2' = R_4' = H$
8. $R_4 = OCH_3, R_3' = F, R_3 = R_2' = R_4' = H$
9. $R_4 = OCH_3, R_3' = Cl, R_3 = R_2' = R_4' = H$
10. $R_4 = R_3' = OCH_3, R_3 = R_2' = R_4' = H$
11. $R_4 = OCH_3, R_3 = R_2' = R_3' = R_4' = H$
12. $R_4 = R_3 = R_2' = R_3' = R_4' = H$
13. $R_4 = Cl, R_2' = F, R_3 = R_3' = R_4' = H$
14. $R_4 = R_2' = Cl, R_3 = R_3' = R_4' = H$
15. $R_4 = Cl, R_2' = OCH_3, R_3 = R_3' = R_4' = H$
16. $R_4 = Cl, R_3 = R_2' = R_3' = R_4' = H$
17. $R_4 = R_2' = F, R_3 = R_3' = R_4' = H$
18. $R_4 = F, R_2' = Cl, R_3 = R_3' = R_4' = H$
19. $R_4 = F, R_2' = OCH_3, R_3 = R_3' = R_4' = H$
20. $R_4 = OCH_3, R_2' = F, R_3 = R_3' = R_4' = H$
21. $R_4 = OCH_3, R_2' = Cl, R_3 = R_3' = R_4' = H$
22. $R_4 = OCH_3, R_4' = F, R_3 = R_2' = R_3' = H$
23. $R_3, R_4 = ——OCH_3—, R_2' = R_3' = R_4' = H$

VI

1. $R_4 = F, R_3' = Cl, R_3 = R_2' = R_4' = H$
2. $R_4 = R_3' = F, R_3 = R_2' = R_4' = H$
3. $R_4 = F, R_3' = OCH_3, R_3 = R_2' = R_4' = H$
4. $R_4 = R_3' = Cl, R_3 = R_2' = R_4' = H$
5. $R_4 = R_2' = F, R_3 = R_3' = R_4' = H$
6. $R_4 = OCH_3, R_2' = Cl, R_3 = R_3' = R_4' = H$

↓ 150~170° C.    ↓ 150~170° C.

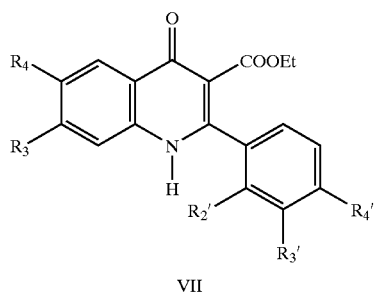

VII

1. $R_4 = F, R_3' = Cl, R_3 = R_2' = R_4' = H$
2. $R_4 = R_3' = F, R_3 = R_2' = R_4' = H$
3. $R_4 = F, R_3' = OCH_3, R_3 = R_2' = R_4' = H$
4. $R_4 = F, R_3 = R_2' = R_3' = R_4' = H$
5. $R_4 = Cl, R_3' = F, R_3 = R_2' = R_4' = H$
6. $R_4 = R_3' = Cl, R_3 = R_2' = R_4' = H$
7. $R_4 = Cl, R_3' = OCH_3, R_3 = R_2' = R_4' = H$
8. $R_4 = OCH_3, R_3' = F, R_3 = R_2' = R_4' = H$
9. $R_4 = OCH_3, R_3' = Cl, R_3 = R_2' = R_4' = H$
10. $R_4 = R_3' = OCH_3, R_3 = R_2' = R_4' = H$
11. $R_4 = OCH_3, R_3 = R_2' = R_3' = R_4' = H$
12. $R_4 = R_3 = R_2' = R_3' = R_4' = H$
13. $R_4 = Cl, R_2' = F, R_3 = R_3' = R_4' = H$
14. $R_4 = R_2' = Cl, R_3 = R_3' = R_4' = H$
15. $R_4 = Cl, R_2' = OCH_3, R_3 = R_3' = R_4' = H$
16. $R_4 = Cl, R_3 = R_2' = R_3' = R_4' = H$
17. $R_4 = R_2' = F, R_3 = R_3' = R_4' = H$
18. $R_4 = F, R_2' = Cl, R_3 = R_3' = R_4' = H$
19. $R_4 = F, R_2' = OCH_3, R_3 = R_3' = R_4' = H$
20. $R_4 = OCH_3, R_2' = F, R_3 = R_3' = R_4' = H$
21. $R_4 = OCH_3, R_2' = Cl, R_3 = R_3' = R_4' = H$
22. $R_4 = OCH_3, R_4' = F, R_3 = R_2' = R_3' = H$
23. $R_3, R_4 = ——OCH_3—, R_2' = R_3' = R_4' = H$

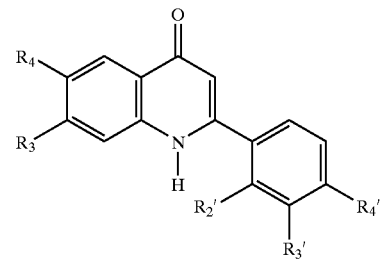

VIII

1. $R_4 = F, R_3' = Cl, R_3 = R_2' = R_4' = H$
2. $R_4 = R_3' = F, R_3 = R_2' = R_4' = H$
3. $R_4 = F, R_3' = OCH_3, R_3 = R_2' = R_4' = H$
4. $R_4 = R_3' = Cl, R_3 = R_2' = R_4' = H$
5. $R_4 = R_2' = F, R_3 = R_3' = R_4' = H$
6. $R_4 = OCH_3, R_2' = Cl, R_3 = R_3' = R_4' = H$

Scheme 3

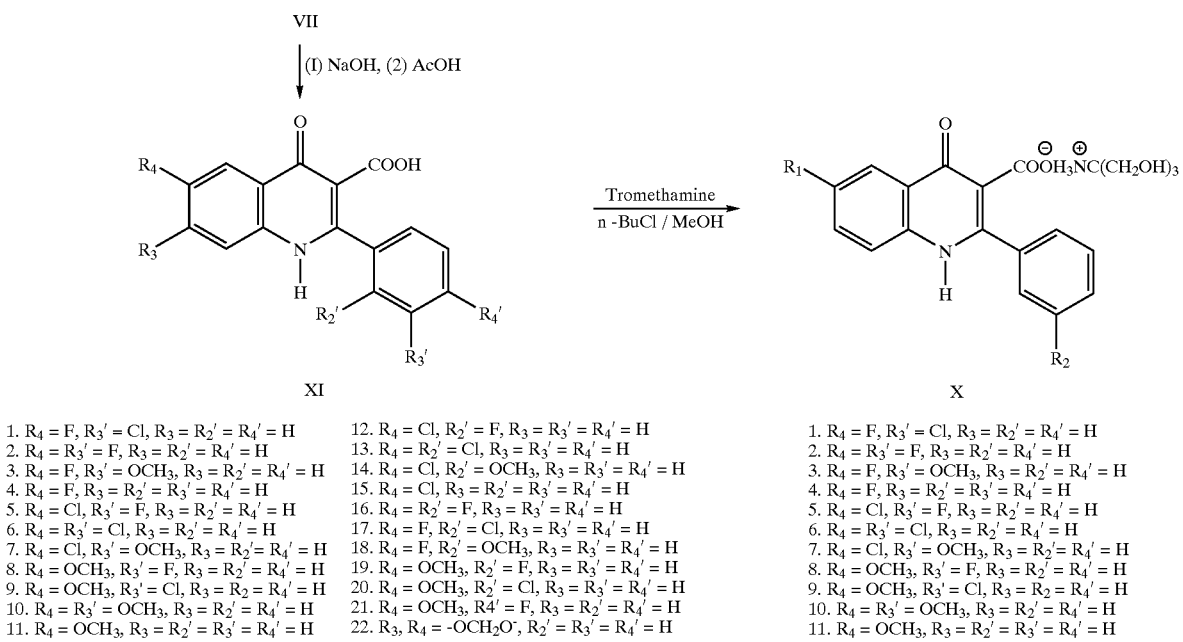

1. $R_4 = F, R_3' = Cl, R_3 = R_2' = R_4' = H$
2. $R_4 = R_3' = F, R_3 = R_2' = R_4' = H$
3. $R_4 = F, R_3' = OCH_3, R_3 = R_2' = R_4' = H$
4. $R_4 = F, R_3 = R_2' = R_3' = R_4' = H$
5. $R_4 = Cl, R_3' = F, R_3 = R_2' = R_4' = H$
6. $R_4 = R_3' = Cl, R_3 = R_2' = R_4' = H$
7. $R_4 = Cl, R_3' = OCH_3, R_3 = R_2' = R_4' = H$
8. $R_4 = OCH_3, R_3' = F, R_3 = R_2' = R_4' = H$
9. $R_4 = OCH_3, R_3' = Cl, R_3 = R_2' = R_4' = H$
10. $R_4 = R_3' = OCH_3, R_3 = R_2' = R_4' = H$
11. $R_4 = OCH_3, R_3 = R_2' = R_3' = R_4' = H$
12. $R_4 = Cl, R_2' = F, R_3 = R_3' = R_4' = H$
13. $R_4 = R_2' = Cl, R_3 = R_3' = R_4' = H$
14. $R_4 = Cl, R_2' = OCH_3, R_3 = R_3' = R_4' = H$
15. $R_4 = Cl, R_3 = R_2' = R_3' = R_4' = H$
16. $R_4 = R_2' = F, R_3 = R_3' = R_4' = H$
17. $R_4 = F, R_2' = Cl, R_3 = R_3' = R_4' = H$
18. $R_4 = F, R_2' = OCH_3, R_3 = R_3' = R_4' = H$
19. $R_4 = OCH_3, R_2' = F, R_3 = R_3' = R_4' = H$
20. $R_4 = OCH_3, R_2' = Cl, R_3 = R_3' = R_4' = H$
21. $R_4 = OCH_3, R_4' = F, R_3 = R_2' = R_4' = H$
22. $R_3, R_4 = -OCH_2O^-, R_2' = R_3' = R_4' = H$

1. $R_4 = F, R_3' = Cl, R_3 = R_2' = R_4' = H$
2. $R_4 = R_3' = F, R_3 = R_2' = R_4' = H$
3. $R_4 = F, R_3' = OCH_3, R_3 = R_2' = R_4' = H$
4. $R_4 = F, R_3 = R_2' = R_3' = R_4' = H$
5. $R_4 = Cl, R_3' = F, R_3 = R_2' = R_4' = H$
6. $R_4 = R_3' = Cl, R_3 = R_2' = R_4' = H$
7. $R_4 = Cl, R_3' = OCH_3, R_3 = R_2' = R_4' = H$
8. $R_4 = OCH_3, R_3' = F, R_3 = R_2' = R_4' = H$
9. $R_4 = OCH_3, R_3' = Cl, R_3 = R_2' = R_4' = H$
10. $R_4 = R_3' = OCH_3, R_3 = R_2' = R_4' = H$
11. $R_4 = OCH_3, R_3 = R_2' = R_3' = R_4' = H$

Experimental Section

Melting points were determined on a Yanaco MP-500D melting point apparatus and are uncorrected. IR spectra were recorded on Shimadzu IR-440 and Nicolet Impact 400 FT-Irspecrophotometers as KBr pellets, NMR spectra were obtained on a Bruker Advance DPX-200 FT-NMR spectrometer in DMSO-$d_6$. The following abbreviations are used: s, singlet; d, doublet; t, triplet; q, quartet; m, multiplet; and br, broad MS spectra were measured with an HP 5995 GC-MS instrument. The UV spectra were recorded on a Shimadzu UV-160A UV-vis recording spectrophotometer as methanolic solutions. Elemental analyses (C, H, N) were performed at China Medical College, Taiwan, and the results were within ±0.4% of the calculated values.

3-Chlorophenyl-N-(4-fluorophenyl)benzamide (III-1)

p-Fluoroaniline (I-1) (11.11 g, 0.1 mol) in 100 ml of toluene at 20±2° C., were added dropwise m-chlorobenzoyl chloride (II-1) (8.81 g, 0.05 mol). After stirred for 3 h, the resulting precipitates were collected and recrytallized from EtOH, and then compound 9 were obtained; colorless needles (9.59 g, 77%); mp 134–136° C.; $^1$H NMR (DMSO-$d_6$) δ 7.18 (2H, dd, J=8.9 Hz, H-3', H-5'), 7.36–7.46 (1H, m, H-4), 7.51–7.62 (1H, m, H-5), 7.74–7.84 (4H, m, H-2, H-6, H-2', H-6'), 10.41 (1H, br, NH); IR (KBr) ν 3330 (—NH), 1650 (—C=O) cm$^{-1}$; MS (M$^+$) m/z 249.7. Anal. calcd C, 62.54; H, 3.63; N, 5.61. Found, C, 62.36; H, 3.64; N, 5.62.

3-Fluorophenyl-N-(4-fluorophenyl)benzamide (III-2): obtained from compound I-1 (11.11 g, 0.1 mol) and compound II-2 (7.93 g, 0.05 mol) as described in the preparation of compound III-1; colorless needles (9.32 g, 80%); mp 147–148° C.; $^1$H NMR (DMSO-$d_6$) δ 7.16 (2H, dd, J=8.8 Hz, H-3', H-5'), 7.34–7.43 (1H, m, H-4), 7.49–7.60 (1H, m, H-5), 7.75–7.86 (4H, m, H-2, H-6, H-2', H-6'), 10.37 (1H, br, NH); IR (KBr) ν 3333 (—NH), 1651 (—C=O) cm$^{-1}$; MS (M$^+$) m/z 233. Anal. calcd C, 66.95; H, 3.89; N, 6.01. Found, C, 67.18; H, 3.88; N, 5.99.

3-Methoxyphenyl-N-(4-fluorophenyl)benzamide (III-3): obtained from compound I-1 (11.11 g, 0.1 mol) and compound II-3 (8.53 g, 0.05 mol) as described in the preparation of compound III-1; colorless needles (7.19 g, 75%); mp 104–105° C.; $^1$H NMR (DMSO-$d_6$) δ 3.83 (3H, s, OCH$_3$), 7.11–7.23 (3H, m, H-4, H-3', H-5'), 7.43 (1H, t, J=7.7 Hz, H-5), 7.47–7.56 (2H, m, H-2, H-6), 7.79 (2H, dd, J=9.1, 5.1 Hz, H-2', H-6'), 10.27 (1H, br, NH); IR (KBr) ν 3305 (—NH), 1650 (—C=O) cm$^{-1}$; MS (M$^+$) m/z 245. Anal. calcd C, 68.56; H, 4.93; N, 5.71. Found, C, 68.79; H, 4.93; N, 5.69.

N-(4-Fluorophenyl)benzamide (III-4): obtained from compound I-1 (11.11 g, 0.1 mol) and compound II-4 (7.03 g, 0.05 mol) as described in the preparation of compound III-1; colorless needles (8.28 g, 77%); mp 167–168° C.; $^1$H NMR (DMSO-$d_6$) δ 7.18 (2H, dd, J=9.0, 9.0 Hz, H-3', H-5'), 7.47–7.58 (3H, m, H-4, H-2', H-6'), 7.80 (2H, m, H-3, H-5), 7.95 (2H, m, H-2, H-6), 10.31(1H, br, NH); IR (KBr) ν 3344 (—NH), 1655 (—C=O) cm$^{-1}$; MS (M$^+$) m/z 215. Anal. calcd C, 72.55; H, 4.68; N, 6.51. Found, C, 72.78; H, 4.67; N, 6.50.

3-Fluorophenyl-N-(4-chlorophenyl)benzamide (III-5): obtained from compound I-2 (12.70 g, 0.1 mol) and compound II-2 (7.93 g, 0.05 mol) as described in the preparation of compound III-1; colorless needles (10.21 g, 82%); mp 156–158° C.; $^1$H NMR (DMSO-$d_6$) δ 7.40 (2H, d, J=8.9 Hz, H-3', H5'), 7.43–7.48 (1H, m, H-5), 7.52–7.60 (1H, m, H-4), 7.71–7.82 (4H, m, H-2, H-6, H-2', H-6'), 10.42 (1H, br, NH); IR (KBr) ν 3320 (—NH), 1656 (—C=O) cm$^{-1}$; MS (M$^+$) m/z 249.7. Anal. calcd C, 62.54; H, 3.63; N, 5.61. Found, C, 62.72; H, 3.64; N, 5.63.

3-Chloro-N-(4-chlorophenyl)benzamide (III-6): obtained from compound II-2 (12.71 g, 0.1 mol) and compound II-1 (8.82 g, 0.05 mol) as described in the preparation of compound III-1; colorless needles (10.64 g, 80%); mp 124–126° C.; $^1$H NMR (DMSO-$d_6$) δ 7.38–7.43 (2H, d, J=8.8 Hz, H-3', H5'), 7.51–7.59 (1H, t, J=7.6 Hz, H-5), 7.63–7.68 (1H, d, J=8.3 Hz, H-4), 7.78–7.82 (2H, d, J=8.8 Hz, H-2', H-6'), 7.87–7.92 (1H, dt, J=1.5, 7.6 Hz, H-6), 7.98–8.00 (1H, t, J=1.6 Hz, H-2), 10.46 (1H, br, NH); IR (KBr) ν 3353 (—NH), 1652 (—C=O) cm$^{-1}$; MS (M$^+$) m/z 266. Anal. calcd C, 58.67; H, 3.41; N, 5.26. Found, C, 58.85; H, 3.42; N, 5.23.

3-Methoxyphenyl-N-(4-chlorophenyl)benzamide (III-7): obtained from compound I-2 (12.72 g, 0.1 mol) and compound II-3 (8.53 g, 0.05 mol) as described in the preparation of compound III-1; colorless needles (9.92 g, 76%); mp 123–124° C.; $^1$H NMR(DMSO-$d_6$) δ 3.99 (3H, s, OCH$_3$), 7.13–7.16 (1H, dd, J=2.4, 8.3 Hz, H-4), 7.38–7.41 (2H, d, J=8.8 Hz, H-2', H-6'), 7.43–7.44 (1H, t, H-5), 7.44–7.45 (1H, s, H-2), 7.50–7.52 (1H, d, J=7.8 Hz, H-6), 7.74–7.77 (2H, d, J=11.7 Hz, H-6); IR (KBr) v 3300 (—NH), 1649 (—C=O) cm$^{-1}$; MS (M$^+$) m/z 261.7. Anal. calcd C, 64.25; H, 4.62; N, 5.35. Found, C, 64.38; H, 4.60; N, 5.37.

3-Fluorophenyl-N-(4-methoxyphenyl)benzamide (III-8): obtained from compound I-3 (12.3 g, 0.1 mol) and compound II-2 (7.93 g, 0.05 mol) as described in the preparation of compound III-1; colorless needles (10.78 g, 88%); mp 161–163° C.; $^1$H NMR (DMSO-$d_6$) δ 3.64 (3H, s, OCH$_3$), 6.83 (2H, d, J=9.1 Hz, H-3', H-5'), 7.26–7.36 (1H, m, H-4), 7.48 (1H, m, H-5), 7.56 (2H, d, J=9.1 Hz, H-2', H-6'), 7.62–7.72 (2H, m, H-2, H-6), 10.10 (1H, br, NH); IR (KBr) v 3320 (—NH), 1650 (—C=O) cm$^{-1}$; MS (M$^+$) m/z 245. Anal. calcd C, 68.56; H, 4.93; N, 5.71. Found, C, 68.37; H, 4.95; N, 5.69.

3-Chlorophenyl-N-(4-methoxyphenyl)benzamide (III-9): obtained from compound I-3 (12.3 g, 0.1 mol) and compound II-1 (8.82 g, 0.05 mol) as described in the preparation of compound III-1; colorless needles (10.57 g, 81%); mp 146–148° C.; $^1$H NMR (DMSO-$d_6$) δ 3.73 (3H, s, OCH$_3$), 6.93 (2H, d, J=9.0 Hz, H-3', H-5'), 7.47–7.51 (1H, m, H-5), 7.58–7.62 (1H, m, H-4), 7.71 (2H, d, J=9.0 Hz, H-2', H-6'), 7.93 (1H, d, J=7.4 Hz, H-6), 8.02 (1H, m, H-2), 10.25 (1H, br, NH); IR (KBr) v 3345 (—NH), 1650 (—C=O)cm$^{-1}$; MS (M$^+$) m/z 227. Anal. calcd C, 64.25; H, 4.62; N, 5.35. Found, C, 64.39; H, 64.39; N, 64.39.

3-Methoxyphenyl-N-(4-methoxyphenyl)benzamide (III-10): obtained from compound I-3 (12.3 g, 0.1 mol) and compound II-3 (8.53 g, 0.05 mol) as described in the preparation of compound III-1; colorless needles (10.02 g, 78%); mp 107–109° C.; $^1$H NMR (DMSO-$d_6$) δ 3.74 (3H, s, 4'-OCH$_3$), 3.83 (3H, s, 3-OCH$_3$), 6.93 (2H, d, J=9.1 Hz, H-3', H-5'), 7.50 (1H, m, H-2), 7.13 (1H, d, J=9.1 Hz, H-4), 7.42 (1H, d, J=7.7 Hz, H-5), 7.55 (1H, d, J=7.7 Hz, H-6), 7.69 (2H, d, J=9.0 Hz, H-2', H-6'), 10.11 (1H, br, NH); IR (KBr) v 3304 (—NH), 1644 (—C=O) cm$^{-1}$; MS (M$^+$) m/z 257. Anal. calcd C, 70.02; H, 5.88; N, 5.44. Found, C, 70.21; H, 5.90; N, 5.45.

N-(4-Methoxyphenyl)benzamide (III-11): obtained from compound I-3 (12.3 g, 0.1 mol) and compound II-4 (7.03 g, 0.05 mol) as described in the preparation of compound III-1; colorless needles (9.65 g, 85%); mp 153–155° C.; $^1$H NMR (DMSO-$d_6$) δ 3.74 (3H, s, OCH$_3$), 6.93 (2H, d, J=9.0 Hz, H-3', H-5'), 7.50–7.57 (3H, m, H-3, H-4, H-5), 7.71 (2H, d, J=9.0 Hz, H-2', H-6'), 7.97 (2H, dd, J=7.4, 1.6 Hz, H-2, H-6), 10.16 (1H, br, NH); IR (KBr) v 3332 (—NH), 1649 (—C=O) cm$^{-1}$; MS (M$^+$) m/z 227. Anal. calcd C, 73.99; H, 5.77; N, 6.16. Found, C, 74.15; H, 5.77; N, 6.15.

N-Phenylbenzamide (III-12): obtained from compound I-4 (9.23 g, 0.1 mol) and compound II-4 (7.03 g, 0.05 mol ) as described in the preparation of compound III-1; needles; (8.13 g, 82%); mp156–158° C.; $^1$H NMR (DMSO-$d_6$) δ 7.07 (1H, dd, J=7.3 Hz, H-4), 7.18–7.50 (5H, m, H-3, H-5, H-3', H-4', H-5'), 7.56 (2H, d, J=7.7Hz, H-2, H-6), 7.77 (2H, d, J=7.3Hz, H-2', H-6'), 7.89 (1H, br, NH); IR (KBr) v3345 (—NH), 1656 (—C=O) cm$^{-1}$; MS m/z 197 (M$^+$). Anal. calcd C, 79.17; H, 5.62; N, 7.10. Found, C, 79.35; H, 5.62; N, 7.08.

N-(4-Chlorophenyl)-2-fluorobenzamide (III-13): obtained from compound I-2 (6.38 g, 0.05 mol) and compound II-6 (3.97 g, 0.025 mol) as described in the preparation of compound III-1; colorless needles (4.86 g, 78%); mp 94.5–96.2° C.; $^1$H NMR (DMSO-$d_6$) δ7.28–7.36 (2H, m, H-3, H-5), 7.40 (2H, d, J=8.8 Hz, H-3', H-5'), 7.52–7.68 (2H, m, H-4, H-6), 7.77 (2H, d, J=8.8 Hz, H-2', H-6'), 10.55 (1H, s, NH); IR (KBr) v 3348 (—NH), 1661 (—C=O) cm$^{-1}$; MS (M$^+$) m/z 249. Anal. calcd C, 62.54; H, 3.63; N, 5.61. Found, C, 62.59; H, 3.61; N, 5.60.

2-Chloro-N-(4-chlorophenyl)benzamide (III-14): obtained from compound II-2 (6.38 g, 0.05 mol) and compound II-5 (4.38 g, 0.025 mol) as described in the preparation of compound III-1; colorless needles (5.10 g, 77%); mp 93.7–95.1° C.; $^1$H NMR (DMSO-$d_6$) δ7.41 (2H, d, J=8.9 Hz, H-3', H-5'), 7.45–7.62 (4H, m, H-3, H-4, H-5, H-6), 7.76 (2H, d, J=8.9 Hz, H-2', H-6'), 10.66 (1H, s, NH); IR (KBr) v 3300 (—NH), 1659 (—C=O) cm$^{-1}$; MS (M$^+$) m/z 265. Anal. calcd C, 58.67; H, 3.41; N, 5.26. Found, C, 58.70; H, 3.39; N, 5.27.

N-(4-Chlorophenyl)-2-methoxybenzamide (III-15): obtained from compound I-2 (6.38 g, 0.05 mol) and compound II-7 (4.27 g, 0.025 mol) as described in the preparation of compound III-1; colorless needles (5.09 g, 78%); mp 56.1–58.7° C.; $^1$H NMR (DMSO-$d_6$) δ3.89 (3H, s, OCH$_3$), 7.06 (1H, dd, J=7.5, 7.5 Hz, H-5), 7.14 (1H, d, J=8.4 Hz, H-3), 7.39 (2H, d, J=8.7 Hz, H-3', H-5'), 7.49 (1H, dd, J=8.4, 7.5 Hz, H-4), 7.67 (1H, d, J=7.5 Hz, H-6), 7.83 (2H, d, J=8.7 Hz, H-2', H-6'), 10.27 (1H, s, NH); IR (KBr) v 3344 (—NH), 1651 (—C=O) cm$^{-1}$; MS (M$^+$) m/z 261. Anal. calcd C, 64.25; H, 4.62; N, 5.35. Found, C, 64.26; H, 4.60; N, 5.34.

N-(4-Chlorophenyl)benzamide (III-16): obtained from compound I-2 (6.38 g, 0.05 mol) and compound II-4 (3.51 g, 0.025 mol) as described in the preparation of compound III-1; colorless needles (4.68 g, 81%); mp 140.9–141.2° C. (dec); $^1$H NMR (DMSO-$d_6$) δ 7.40 (2H, d, J=8.8 Hz, H-3', H-5'), 7.48–7.59 (3H, m, H-3, H-4, H-5), 7.84 (2H, d, J=8.8 Hz, H-2', H-6'), 7.95 (2H, d, J=7.8 Hz, H-2, H-6), 10.38 (1H, s, NH); IR (KBr) v 3350 (—NH), 1655 (—C=O) cm$^{-1}$; MS (M$^+$) m/z 231. Anal. calcd C, 67.40; H, 4.35; N, 6.05. Found, C, 67.39; H, 4.36; N, 6.06.

2-Fluoro-N-(4-fluorophenyl)benzamide (III-17): obtained from compound I-1 (5.56 g, 0.05 mol) and compound II-6 (3.97 g, 0.025 mol) as described in the preparation of compound III-1; colorless needles (4.66 g, 80%); mp 102.0–104.5° C.; $^1$H NMR (DMSO-$d_6$) δ 7.19 (2H, dd, J=9.0, 9.0 Hz, H-3', H-5'), 7.28–7.38 (2H, m, H-3, H-5), 7.52–7.70 (2H, m, H-4, H-6), 7.75 (2H, dd, J=9.0, 5.1 Hz, H-2', H-6'), 10.46 (1H, s, NH); IR (KBr) v 3346 (—NH), 1653 (—C=O) cm$^{-1}$; MS (M$^+$) m/z 233. Anal. calcd C, 66.95; H, 3.89; N, 6.01. Found; H, 66.91; H, 3.88; N, 6.03.

2-Chloro-N-(4-fluorophenyl)benzamide (III-18): obtained from compound I-1 (5.56 g, 0.05 mol) and compound II-5 (4.38 g, 0.025 mol) as described in the preparation of compound III-1; colorless needles (4.73 g, 76%); mp 93.3–96.2° C.; $^1$H NMR (DMSO-$d_6$) δ 7.19 (2H, dd, J=8.8, 8.8 Hz, H-3', H-5'), 7.40–7.61 (4H, m, H-3, H-4, H-5, H-6), 7.76 (2H, dd, J=8.8, 5.1 Hz, H-2', H-6'), 10.58 (1H, s, NH); IR (KBr) v 3288 (—NH), 1657 (—C=O) cm$^{-1}$; MS (M$^+$) m/z 249. Anal. calcd C, 62.54; H, 3.63; N, 5.61. Found, C, 62.58; H, 3.64; N, 5.59.

N-(4-Fluorophenyl)-2-methoxybenzamide (III-19): obtained from compound I-1 (5.56 g, 0.05 mol) and compound II-7 (4.27 g, 0.025 mol) as described in the preparation of compound III-1; colorless needles (4.84 g, 79%); mp 79.6–80.2° C.; $^1$H NMR (DMSO-$d_6$) δ 3.89 (3H, s, OCH$_3$), 7.05 (1H, dd, J=7.5, 7.5 Hz, H-5), 7.13–7.21 (2H, m, H-3, H-3', H-5'), 7.49 (1H, dd, J=8.3, 7.5 Hz, H-4), 7.63 (1H, d, J=7.5 Hz, H-6), 7.77 (2H, dd, J=8.9, 5.1 Hz, H-2', H-6'), 10.16 (1H, s, NH); IR (KBr) v 3329 (—NH), 1647 (—C=O) cm$^{-1}$; MS (M$^+$) m/z 245. Anal. calcd C, 68.56; H, 4.93; N, 5.71. Found, C, 68.55; H, 4.94; N, 5.72.

2-Fluoro-N-(4-methoxyphenyl)benzamide (III-20): obtained from compound I-3 (6.16 g, 0.05 mol) and compound II-6 (3.97 g, 0.025 mol) as described in the preparation of compound III-1; colorless needles (4.72 g, 77%); mp 83.1–84.3° C.; $^1$H NMR (DMSO-d$_6$) δ 3.74 (3H, s, OCH$_3$), 6.93 (2H, d, J=9.0 Hz, H-3', H-5'), 7.28–7.37 (2H, m, H-3, H-5), 7.53–7.62 (1H, m, H-4), 7.62–7.70 (3H, m, H-6, H-2', H-6'), 10.26 (1H, s, NH); IR (KBr) v 3364 (—NH), 1647 (—C=O) cm$^{-1}$; MS (M$^+$) m/z 245. Anal. calcd C, 68.56; H, 4.93; N, 5.71. Found, C, 68.55; H, 4.91; N, 5.70.

2-Chloro-N-(4-methoxyphenyl)benzamide (III-21): obtained from compound I-3 (6.16 g, 0.05 mol) and compound II-5 (4.38 g, 0.025 mol) as described in the preparation of compound III-1; colorless needles (4.89 g, 75%); mp 113.2–114.7° C.; $^1$H NMR (DMSO-d$_6$) δ 3.74 (3H, s, OCH$_3$), 6.94 (2H, d, J=9.0 Hz, H-3', H-5'), 7.44–7.60 (4H, m, H-3, H-4, H-5, H-6), 7.67 (2H, d, J=9.0 Hz, H-2', H-6'), 10.38 (1H, s, NH); IR (KBr) v 3290 (—NH), 1655 (—C=O) cm$^{-1}$; MS (M$^+$) m/z 261. Anal. calcd C, 64.25; H, 4.62 ; N, 5.35. Found, C, 64.22; H, 4.63; N, 5.33.

2-Methoxy-N-(4-methoxyphenyl)benzamide (III-22): obtained from compound I-3 (6.16 g, 0.05 mol) and compound II-7 (4.27 g, 0.025 mol) as described in the preparation of compound III-1; colorless needles (5.01 g, 78%); mp 49.5–51.2° C.; $^1$H NMR (DMSO-d$_6$) δ 3.72 (3H, s, 4'-OCH$_3$), 3.88 (3H, s, 2-OCH$_3$), 6.90 (2H, d, J=9.0 Hz, H-3', H-5'), 7.04 (1H, dd, J=7.4,7.4 Hz, H-5), 7.14 (1H, d, J=8.3 Hz, H-3), 7.47 (1H, dd, J=8.3, 7.4 Hz, H-4), 7.61–7.67 (3H, m, H-6, H-2', H-6'), 9.96 (1H, s, NH),; IR (KBr) v 3344 (—NH), 1661 (—C=O) cm$^{-1}$; MS (M$^+$) m/z 257. Anal. calcd C, 70.02; H, 5.88; N, 5.44. Found, C, 70.00; H, 5.87; N, 5.43.

4-Fluoro-N-(4-methoxyphenyl)benzamide (III-23): obtained from compound I-3 (6.16 g, 0.05 mol) and compound II-8 (3.97 g, 0.025 mol) as described in the preparation of compound III-1; colorless needles (5.02 g, 82%); mp 170.6–172.1° C.; $^1$H NMR (DMSO-d$_6$) δ 3.73 (3H, s, OCH$_3$), 6.92 (2H, d, J=9.0 Hz, H-3', H-5'), 7.33 (2H, dd, J=8.8, 8.8 Hz, H-3, H-5), 7.66 (2H, d, J=9.0 Hz, H-2', H-6'), 8.03 (2H, dd, J=8.8, 5.5 Hz, H-2, H-6), 10.15 (1H, s, NH); IR (KBr) v 3329 (—NH), 1651 (—C=O) cm$^{-1}$; MS (M$^+$) m/z 245. Anal. calcd C, 68.56; H, 4.93; N, 5.71. Found, C, 68.52; H, 4.92; N, 5.70.

2-Chloro-N-phenylbenzamide (III-24): obtained from compound I-4 (4.66 g, 0.05 mol) and compound II-5 (4.38 g, 0.025 mol) as described in the preparation of compound III-1; colorless needles (4.85 g, 84%); mp 96.4–98.3° C.; $^1$H NMR (DMSO-d$_6$) δ 7.11 (1H, dd, J=7.4, 7.4 Hz, H-4'), 7.36 (2H, dd, J=8.1, 7.4 Hz, H-3', H-5'), 7.44–7.61 (4H, m, H-3, H-4, H-5, H-6), 7.75 (2H, d, J=8.1 Hz, H-2', H-6'), 10.53 (1H, s, NH),; IR (KBr) v 3265 (—NH), 1649 (—C=O) cm$^{-1}$; MS (M$^+$) m/z 231. Anal. calcd C, 67.40; H, 4.35 ; N, 6.05. Found, C, 67.38; H, 4.33; N, 6.06.

N-[(3,4-Methylenedioxy)phenyl]benzamide (III-25): obtained from compound I-5 (6.86 g, 0.05 mol) and compound II-4 (3.51 g, 0.025 mol) as described in the preparation of compound III-1; colorless needles (4.76 g, 79%); mp 109.6–111.8° C.; $^1$H NMR (DMSO-d$_6$) δ 6.00 (2H, s, OCH$_2$O), 6.89 (1H, d, J=8.4 Hz, H-5'), 7.21 (1H, dd, J=8.4, 2.0 Hz, H-6'), 7.47 (1H, d, J=2.0 Hz, H-2'), 7.50–7.57 (3H, m, H-3, H-4, H-5), 7.93 (2H, dd, J=8.0, 1.9 Hz, H-2, H-6), 10.17 (1H, s, NH),; IR (KBr) v 3312 (—NH), 1645 (—C=O) cm$^{-1}$; MS (M$^+$) m/z 241. Anal. calcd C, 69.70; H, 4.60; N, 5.81. Found, C, 69.68; H, 4.59; N, 5.80.

N-[1-(3-chlorophenyl)-2,2-diethoxycarbonylvinyl]-N-(4-fluorophenyl)amine (V-1), N-[1-(3-chloropheny)-2-ethoxycarbonylvinyl]-N-(4-fluorophenyl)amine (VI-1), Ethyl 3'-chloro-6-fluoro-phenyl-4-quinolone-3-carboxylate (VII-1) and 3'-chloro-6-fluoro-2-phenyl-4-quinolone (VIII-1)

Method A

PCl$_5$ (2.24 g, 0.01 mol) was added into compound III-1 (2.50 g, 0.01 mol) and the mixture was heated to 110° C., stirred for additional 1 h, and then evaporated under vacuum to yield carboximidoyl chloride (IV-1) as viscous liquids.

Meanwhile, diethyl malonate (4.8 g, 0.03 mol) was introduced dropwise into the solution of Na$^o$ (0.72 g, 0.03 mol) in absolute ethanol (50 ml), at 20±2° C. The mixture was stirred for 1 h at 50±2° C. Subsequent removal of ethanol under vacuum afforded sodium diethyl moloante as gel.

Then compound IV-1 was dissolved in toluene (20 ml) and added into the suspension of sodium diethyl moloante in toluene (20 ml). The resulted mixture was allowed to react 4 hr at 110° C. After filtration the filtrate was concentrated and extracted with ether, washed with water, dried over MgSO$_4$ and concentrated under vacuum to yield V-1 and VI-1 as yellowish, viscous liquid.

Without further purification, the viscous liquid was heated for 4 h at 170° C. to give yellowish solid that was purified further by column chromatography (silica gel, 100:1 CHCl$_3$-EtOH) and recrystallized from CHCl$_3$-EtOH to produce compounds VII-1 (1.21 g, 35%) and VII-1 (0.41 g, 15%).

Compound VII-1: colorless needles; mp 215–217° C.; $^1$H NMR (DMSO-d$_6$) δ 0.92 (3H, t, J=7.2 Hz, CH$_3$), 3.96 (2H, q, J=7.2 Hz, CH$_2$), 7.44–7.61 (3H, m, aromatic), 7.71–7.92 (4H, m, aromatic), 12.30 (1H, br, NH); IR (KBr) v 1723, 1615 (—C=O) cm$^{-1}$; MS (M$^+$) m/z 345.5. Anal. calcd C, 62.53; H, 3.79; N, 4.05. Found, C, 62.79; H, 3.80; N, 4.04.

Compound VIII-1: amorphous colorless; mp 271–289° C. (dec); $^1$H NMR (DMSO-d$_6$) δ 6.38 (1H, s, H-3), 7.57–7.81 (6H, m, H-5, H-7, H-8, H-4', H-5', H-6'), 7.92 (1H, s, H-2'), 11.90 (1H, br, NH); IR (KBr) v 1630 (—C=O) cm$^{-1}$; MS (M$^+$) m/z 273. Anal. calcd C, 65.83; H, 3.31; N, 5.1. Found, C, 65.66; H, 3.29; N, 5.11.

Method B

Following the same synthetic route of method A for preparating compounds V-1 and VI-1. The yellowish viscous liquid was chromatographed on silica gel with CHCl$_3$ as eluant to give N-[1-(3-chlorophenyl)-2,2-diethoxycarbonylvinyl]-N-(4-fluoro phenyl) amine (V-1) (1.84 g, 47%) and N-[1-(3-chloropheny)-2-ethoxycarbonylvinyl]-N-(4-fluorophenyl)amine (VI-1) (1.09 g, 34%). Compound V-1 (1.17 g, 3 mmol) was heated for 4 hr at 170° C. to give yellowish solid, that was purified by column chromatography (silica gel, CHCl$_3$-EtOH) to product compound VII-1 (0.84 g, 81%). From compound VI-1 (0.96 g, 3 mmol), the same procedure used for the synthesis of compound VII-1 gave product VIII-1 (0.60 g, 73%).

Compound V-1: mp 70–72° C.; $^1$H NMR (DMSO-d$_6$) δ 0.92 (3H, t, J=7.2 Hz, CH$_3$), 1.30 (3H, t, J=7.2 Hz, CH$_3$), 3.90 (2H, q, J=7.2 Hz, —CH$_2$—), 4.28 (2H, q, J=7.2 Hz, —CH$_2$—), 6.67–6.78 (2H, m, H-3, H-5), 6.81–6.83 (2H, m, H-2, H-6), 7.20–7.28 (2H, m, H-4', H-5'), 7.77–7.90 (2H, m, H-2', H-6'), 11.30 (1H, br, NH); IR (KBr) v 1720, 1725 (—C=O) cm$^{-1}$; MS (M$^+$) m/z 391.5. Anal. calcd C, 61.31; H, 4.89; N, 3.57. Found, C, 61.42; H, 4.91; N, 3.56.

Compound VI-1: mp 52–54° C.; $^1$H NMR (DMSO-d$_6$) δ 1.31 (3H, t, J=7.2 Hz, CH$_3$), 4.20 (2H, q, J=7.2 Hz, —CH$_2$—), 4.99 (1H, s, =CH$_2$—), 6.64–6.67 (2H, m, H-3, H-5), 6.78–6.83 (2H, m, H-2, H-6), 7.16–7.18 (2H, m, H-4', H-5'), 7.27–7.36 (1H, m, H-6'), 7.79–7.80 (1H, m, H-2'), 12.56 (1H, br, NH); IR (KBr) ν 1720 (—C=O) cm$^{-1}$; MS (M$^+$) m/z 391.5. Anal. calcd C, 63.86; H, 4.73; N, 4.38. Found, C, 63.79; H, 4.74; N, 4.38.

Ethyl 3',6-difluoro-2-phenyl-4-quinolone-3-carboxylate (VII-2) and 3',6-difluoro-2-phenyl-4-quinolone (VIII-2): obtained from compound III-2 (2.33 g, 0.01 mol) using the procedure of method A for preparing compounds VII-1 and VII-2.

Compound VII-2: colorless needles (1.21 g, 38%); mp 209–220° C. (dec); $^1$H NMR (DMSO-d$_6$) δ 0.93 (3H, t, J=7.2 Hz, CH$_3$), 3.98 (2H, q, J=7.2 Hz, CH$_2$), 7.38–7.49 (3H, m, aromatic), 7.59–7.78 (4H, m, aromatic), 12.28 (1H, br, NH); IR (KBr) ν 3228 (—NH), 1722, 1612 (—C=O) cm$^{-1}$; MS (M$^+$) m/z 329. Anal. calcd C, 65.65; H, 3.98; N, 4.25. Found, C, 65.88; H, 3.97; N, 4.26.

Compound VIII-2: amorphous colorless (0.33 g, 13%); mp 252–278° C. (dec); $^1$H NMR (DMSO-d$_6$) δ 6.43 (1H, s, H-3), 7.40 (1H, dd, J=8.2, 7.4 Hz, H-7), 7.57–7.85 (6H, m, H-5, H-8, H-2', H-4', H-5', H-6'), 11.87 (1H, br, NH); IR (KBr) ν 1635 (—C=O) cm$^{-1}$; MS (M$^+$) m/z 257. Anal. calcd C, 70.04; H, 3.53; N, 5.45. Found, C, 69.78; H, 3.53; N, 5.46.

Ethyl 3'-methoxy-6-fluoro-2-phenyl-4-quinolone-3-carboxylate (VII-3) and 3'-methoxy-6-fluoro-2-phenyl-4-quinolone (VIII-3): obtained from compound III-3 (2.45 g, 0.01 mol) using the procedure of method A for preparing compounds VII-1 and VIII-1.

Compound VII-3: colorless needles (1.09 g, 32%); mp 214–216° C.; $^1$H NMR (DMSO-d$_6$) δ 0.95 (3H, t, J=7.2 Hz, CH$_3$), 3.86 (3H, s, OCH$_3$), 4.00 (2H, q, J=7.2 Hz, CH$_2$), 7.12–7.15 (3H, m, H-2', H-4', H-6'), 7.47 (1H, t, J=4.1 Hz, H-5'), 7.63 (1H, ddd, J=8.4, 2.9 Hz, H-7), 7.75–7.79 (2H, m, H-5, H-8), 12.19 (1H, br, NH); IR (KBr) ν 1711 (—C=O) cm$^{-1}$; MS (M$^+$) m/z 341. Anal. calcd C, 66.86; H, 4.73; N, 4.10. Found, C, 67.01; H, 4.73; N, 4.11.

Compound VIII-3: amorphous colorless (0.32 g, 12%); mp 236° C. (dec); $^1$H NMR (DMSO-d$_6$) δ 3.86 (3H, s, OCH$_3$), 6.43 (1H, s, H-3), 7.53–7.63 (3H, m, H-7, H-4', H-5'), 7.68–7.91 (4H, m, H-5, H-8, H-2', H-6'), 11.91 (1H, br, NH); IR (KBr) ν 1631 (—C=O) cm$^{-1}$; MS (M$^+$) m/z 269. Anal. calcd C, 71.37; H, 4.49; N, 5.20. Found, C, 71.44; H, 4.47; N, 5.21.

Ethyl 3',6-dichloro-phenyl-4-quinolone-3-carboxylate (VII-6) and 3',6-dichloro-2-phenyl-4-quinolone (VIII-4): obtained from compound III-6 (8.12 g, 0.03 mol) using the procedure of method A for preparing compounds VII-1 and VIII-1.

Compound VII-6: colorless needles (4.89 g, 45%); mp 210–228° C. (dec); $^1$H NMR (DMSO-d$_6$) δ 0.93 (3H, t, J=7.1 Hz, CH$_3$), 3.99 (2H, q, J=7.1 Hz, CH$_2$), 7.50–7.77 (6H, m, H-7, H-8, H-2', H-4', H5', H-6'), 8.04 (1H, s, H-5), 12.31 (1H, br, NH); IR (KBr) ν 1720, 1631 (—C=O) cm$^{-1}$; MS (M$^+$) m/z 362. Anal. calcd C, 59.69; H, 3.62; N, 3.87. Found, C, 59.84; H, 3.63; N, 3.87.

Compound VIII-4: amorphous colorless (0.46 g, 16%); mp 275–286° C. (dec); $^1$H NMR (DMSO-d$_6$) δ 6.47 (1H, s, H-3), 7.59–7.80 (5H, m, H-2', H-4', H-5', H-6', H-8), 7.93 (1H, m, H-7), 7.80 (1H, m, H-5); IR (KBr) ν 1636 (—C=O) cm$^1$; MS (M$^+$) m/z 290. Anal. calcd C, 62.09; H, 3.13; N, 4.83. Found, C, 62.30; H, 3.12; N, 4.83.

Ethyl 2',6-difluoro-2-phenyl-4-quinolone-3-carboxylate (VII-17) and 2',6-difluoro-2-phenyl-4-quinolone (VIII-5): obtained from compound III-17 (2.33 g, 0.01 mol) using the procedure of method A for preparing compounds VII-17 and VIII-5.

Compound VII-17: colorless needles (0.82 g, 25%); mp 207.9–209.1° C. (dec.); $^1$H NMR (DMSO-d$_6$) δ 0.85 (3H, t, J=7.0 Hz, CH$_3$), 3.93 (2H, q, J=7.0 Hz, CH$_2$), 7.33–7.46 (2H, m, H-3', H-5'), 7.50–7.75 (4H, m, H-7, H-8, H-4', H-6'), 7.79 (1H, dd, J=9.1, 2.6 Hz, H-5), 12.45 (1H, s, NH),; IR (KBr) ν 1715, 1618 (—C=O) cm$^{-1}$; MS (M$^+$) m/z 329. Anal. calcd C, 65.65; H, 3.98; N, 4.25. Found, C, 65.62; H, 3.99; N, 4.24.

Compound VIII-5: amorphous colorless (0.46 g, 18%); mp 267.2–268.7° C.; $^1$H NMR (DMSO-d$_6$) δ 6.19 (1H, s, H-3), 7.36–7.49 (2H, m, H-3', H-5'), 7.55–7.78 (5H, m, H-5, H-7, H-8, H-4', H-6'), 12.08 (1H, s, NH); IR (KBr) ν 3242 (—NH), 1603 (—C=O) cm$^{-1}$; MS (M$^+$) m/z 257. Anal. calcd C, 70.04; H, 3.53; N, 5.45. Found, C, 70.01; H, 3.50; N, 5.41.

Ethyl 2'-chloro-6-methoxy-2-phenyl-4-quinolone-3-carboxylate (VII-21) and 2'-chloro-6-methoxy-2-phenyl-4-quinolone (VIII-6): obtained from compound III-21 (2.61 g, 0.01 mol) using the procedure of method A for preparing compounds VII-21 and VIII-6.

Compound VII-21: colorless needles (1.54 g, 43%); mp 167.2–168.8° C.; $^1$H NMR (DMSO-d$_6$) δ 0.80 (3H, t, J=7.0 Hz, CH$_3$), 3.86 (3H, s, OCH$_3$), 3.87 (2H, q, J=7.0 Hz, CH$_2$), 7.36 (1H, dd, J=9.0, 2.9 Hz, H-7), 7.46–7.66 (6H, m, H-5, H-8, H-3', H-4', H-5', H-6'), 12.25 (1H, s, NH); IR (KBr) ν 1724, 1618 (—C=O) cm$^{-1}$; MS (M$^+$) m/z 357. Anal. calcd C, 63.78; H, 4.51; N, 3.91. Found, C, 3.80; H, 4.50; N, 3.90.

Compound VIII-6: amorphous colorless (0.43 g, 15%); mp 270.9–272.2° C.; $^1$H NMR (DMSO-d$_6$) δ 3.85 (3H, s, OCH$_3$), 5.99 (1H, s, H-3), 7.32 (1H, dd, J=9.0, 2.9 Hz, H-7), 7.50–7.68 (6H, m, H-5, H-8, H-3', H-4', H-5', H-6'), 11.96 (1H, s, NH); IR (KBr) ν 3246 (—NH), 1605 (—C=O) cm$^{-1}$; MS (M$^+$) m/z 285. Anal. calcd C, 67.26; H, 4.23; N, 4.90. Found, C, 67.27; H, 4.21; N, 4.88.

Ethyl 6-fluoro-2-phenyl-4-quinolone-3-carboxylate (VII-4)

Following the procedure of method A for preparing compound VII-1, product VII-4 was obtained; colorless needles (4.29 g, 46%); mp 277–279° C.; $^1$H NMR (DMSO-d$_6$) δ 0.89 (3H, t, J=7.0 Hz, CH$_3$), 3.96 (2H, q, J=7.0 Hz, CH$_2$), 7.56–7.67 (5H, m, H-7, H-8, H-3', H-4', H-5'), 7.73–7.79 (3H, m, H-5, H-2', H-6'), 12.25 (1H, br, NH); IR (KBr) ν 3232 (—NH), 1720 (—C=O) cm$^{-1}$; MS (M$^+$) m/z 311. Anal. calcd C, 69.45; H, 4.53; N, 4.50. Found, C, 69.24; H, 4.54; N, 4.48.

Ethyl 3'-fluoro-6-chloro-2-phenyl-4-quinolone-3-carboxylate (VII-5)

Following the procedure of method A for preparing compound VII-1, product VII-5 was obtained; colorless needles (5.91 g, 57%); mp 237–238° C.; $^1$H NMR (DMSO-d6) δ 0.92 (3H, t, J=7.1 Hz, CH$_3$), 3.98 (2H, q, J=7.1 Hz, CH$_2$), 7.37–7.67 (4H, m, H-2', H-4', H-5', H-6'), 7.72–7.76 (2H, m, H-7, H-8), 8.05 (1H, d, J=2.2 Hz, H-5); IR (KBr) ν 1715, 1630 (—C=O) cm$^{-1}$; MS (M$^+$) m/z 345.8. Anal. calcd C, 62.53; H, 3.79; N, 4.05. Found, C, 62.59; H, 3.80; N, 4.07.

Ethyl 3'-methoxy-6-chloro-2-phenyl-4-quinolone-3-carboxylate (VII-7)

Following the procedure of method A for preparing compound VII-1, product VII-7 was obtained; colorless needles (5.80 g, 54%); mp 211–236° C. (dec); $^1$H NMR (DMSO-d$_6$) δ 0.80 (3H, t, J=7.2 Hz, CH$_3$), 3.60 (3H, s, OCH$_3$), 3.86 (2H, q, J=7.2 Hz, CH$_2$), 6.66 (1H, m, H-6'), 6.95–7.10 (3H, m, H-2', H-4', H-5'), 7.49 (1H, dd, J=8.9, 2.3 Hz, H-7), 7.78 (1H, d, J=8.9 Hz, H-8), 7.87 (1H, d, J=2.3 Hz, H-5); IR (KBr) ν 1712 (—C=O) cm$^{-1}$; MS (M$^+$) m/z 357.8. Anal. calcd C, 63.78; H, 4.51; N, 3.92. Found, C, 64.01; H, 4.53; N, 3.91.

Ethyl 3'-fluoro-6-methoxy-2-phenyl-4-quinolone-3-carboxylate (VII-8)

Following the procedure of method A for preparing compound VII-1, product VII-8 was obtained; colorless needles (6.44 g, 63%); mp 211–214° C.; $^1$H NMR (DMSO-$d_6$) δ 0.93 (3H, t, J=7.2 Hz, CH$_3$), 3.85 (3H, s, OCH$_3$), 3.98 (2H, q, J=7.1 Hz, CH$_2$), 7.34–7.48 (4H, m, H-2', H-4', H-5', H-6'), 7.51 (1H, d, J=2.9 Hz, H-5), 7.54–7.57 (1H, m, H-7), 7.64 (1H, d, J=9.1 Hz, H-8), 12.13 (1H, br-s, NH); IR (KBr) v 1709, 1632 (—C=O) cm$^1$; MS (M$^+$) m/z 341. Anal. calcd C, 66.86; H, 4.73; N, 4.10. Found, C, 66.99; H, 4.74; N, 4.09.

Ethyl 3'-chloro-6-methoxy-2-phenyl-4-quinolone-3-carboxylate (VII-9)

Following the procedure of method A for preparing compound VII-1, product VII-9 was obtained; colorless needles (6.65 g, 62%); mp 193–210° C. (dec); $^1$H NMR (DMSO-$d_6$) δ 0.90 (3H, t, J=7.1 Hz, CH$_3$), 3.82 (3H, s, OCH$_3$), 3.96 (2H, q, J=7.1 Hz, CH$_2$), 7.37–7.52 (4H, m, H-2', H-4', H-5', H-6'), 7.48 (1H, d, J=2.9 Hz, H-5), 7.36 (1H, dd, J=9.0, 2.9 Hz, H-7), 7.57 (1H, d, J=9.1 Hz, H-8), 12.12 (1H, br-s, NH); IR (KBr) v 1712 (—C=O) cm$^1$; MS (M$^+$) m/z 357.8. Anal. calcd C, 63.78; H, 4.51; N, 3.92. Found, C, 63.55; H, 4.52; N, 3.94.

Ethyl 3',6-dimethoxy-2-phenyl-4-quinolone-3-carboxylate (VII-10)

Following the procedure of method A for preparing compound VII-1, product VII-10 was obtained; colorless needles (6.25 g, 59%); mp 242–243° C. (dec); $^1$H NMR (DMSO-$d_6$) δ 0.93 (3H, t, J=7.2 Hz, CH$_3$), 3.79 (3H, s, OCH$_3$), 3.83 (3H, s, OCH$_3$), 3.97 (2H, q, J=7.1 Hz, CH$_2$), 7.08–7.13 (3H, m, H-2', H-4', H-6'), 7.35 (1H, dd, J=9.1, 2.9 Hz, H-7), 7.44 (1H, t, J=7.9 Hz, H-5'), 7.51 (1H, d, J=2.8 Hz, H-5), 7.65 (1H, d, J=9.2 Hz, H-8), 12.10 (1H, s, NH); IR (KBr) v 1731 (—C=O) cm$^1$; MS (M$^+$) m/z 353. Anal. calcd C, 67.98; H, 5.42; N, 3.96. Found, C, 68.19; H, 5.41; N, 3.95.

Ethyl 6-methoxy-2-phenyl-4-quinolone-3-carboxylate (VII-11)

Following the procedure of method A for preparing compound VII-1, product VII-11 was obtained; colorless needles (5.72 g, 59%); mp 225–227° C.; $^1$H NMR (DMSO-$d_6$) δ 0.89 (3H, t, J=7.1 Hz, CH$_3$), 3.84 (3H, s, OCH$_3$), 3.94 (2H, q, J=7.1 Hz, CH$_2$), 7.36 (1H, dd, J=9.0, 2.9 Hz, H-7), 7.51 (1H, d, J=2.9 Hz, H-5), 7.54 (5H, m, H-2', H-3', H-4', H-5', H-6'), 7.65 (1H, d, J=9.0 Hz, H-8), 12.08 (1H, br, NH); IR (KBr) v 1716 (—C=O) cm$^1$; MS (M$^+$) m/z 323.4. Anal. calcd C, 70.58; H, 5.30; N, 4.33. Found, C, 70.70; H, 5.29; N, 4.34.

Ethyl 2-phenyl-4-quinolone-3-carboxylate (VII-12)

Following the procedure of method A for preparing compound VII-1, product VII-12 was obtained; colorless needles (4.22 g, 48%) mp 211–213° C. (dec); $^1$H NMR (DMSO-$d_6$) δ 0.90 (3H, t, J=7.0 Hz, CH$_3$), 3.95 (2H, q, J=7.0 Hz, CH$_2$), 7.35–7.48 (1H, m, H-6), 7.56 (5H, m, H-3', H-4', H-5', H-7, H-8), 7.69 (2H, m, H-2', H-6'), 8.11 (1H, d, J=8.0 Hz, H-5), 12.08 (1H, br, NH); IR (KBr) v 1719, 1626 (—C=O) cm$^{-1}$; MS m/z 293 (M$^+$). Anal. calcd C, 73.71; H, 5.15; N, 4.78. Found, C, 73.60; H, 5.15; N, 4.79.

Ethyl 6-chloro-2'-fluoro-2-phenyl-4-quinolone-3-carboxylate (VII-13)

Following the procedure of method A for preparing compound VII-1, product VII-13 (0.97 g, 28%) was obtained; colorless needles; mp 239.7–241.2° C.; $^1$H NMR (DMSO-$d_6$) δ 0.84 (3H, t, J=7.0 Hz, CH$_3$), 3.92 (2H, q, J=7.0 Hz, CH$_2$), 7.33–7.67 (5H, m, H-8, H-3', H-4', H-5', H-6'), 7.78 (1H, dd, J=8.9, 2.2 Hz, H-7), 8.07 (1H, d, J=2.2 Hz, H-5), 12.48 (1H, s, NH); IR (KBr) v 1716, 1623 (—C=O) cm$^{-1}$; MS (M$^+$) m/z 345. Anal. calcd C, 62.53; H, 3.79; N, 4.05. Found, C, 62.50; H. 3.77; N, 4.07.

Ethyl 2',6-dichloro-2-phenyl-4-quinolone-3-carboxylate (VII-14)

Following the procedure of method A for preparing compound VII-1, product VII-14 (1.08 g, 30%) was obtained; colorless needles; mp 232.3–234.2° C. (dec.); $^1$H NMR (DMSO-$d_6$) δ 0.79 (3H, t, J=7.0 Hz, CH$_3$), 3.87 (2H, q, J=7.0 Hz, CH$_2$), 7.47–7.67 (5H, m, H-8, H-3', H-4', H-5', H-6'), 7.76 (1H, dd, J=8.8, 2.4 Hz, H-7), 8.08 (1H, d, J=2.4 Hz, H-5), 12.49 (1H, s, NH); IR (KBr) v 1726, 1623 (—C=O) cm$^{-1}$; MS (M$^+$) m/z 361. Anal. calcd C, 59.69; H, 3.62 ; N, 3.87. Found, C, 59.70; H, 3.61; N, 3.89.

Ethyl 6-chloro-2'-methoxy-2-phenyl-4-quinolone-3-carboxylate (VII-15)

Following the procedure of method A for preparing compound VII-1, product VII-15 (1.18 g, 33%) was obtained; colorless needles; mp 221.7–224.0° C.; $^1$H NMR (DMSO-$d_6$) δ 0.84 (3H, t, J=7.0 Hz, CH$_3$), 3.76 (3H, s, OCH$_3$), 3.90 (2H, q, J=7.0 Hz, CH$_2$), 7.07 (1H, dd, J=7.4, 7.4 Hz, H-5'), 7.16 (1H, d, J=8.4 Hz, H-3'), 7.36 (1H, dd, J=7.4, 1.1 Hz, H-6'), 7.51 (1H, ddd, J=8.4, 7.4, 1.1 Hz, H-4'), 7.66 (1H, d, J=8.9 Hz, H-8), 7.74 (1H, dd, J=8.9, 2.2 Hz, H-7), 8.07 (1H, d, J=2.2 Hz, H-5), 12.26 (1H, s, NH),; IR (KBr) v 1722, 1626 (—C=O) cm$^{-1}$; MS (M$^+$) m/z 357. Anal. calcd C, 63.78; H, 4.51; N, 3.91. Found, C, 63.75; H, 4.49; N, 3.90.

Ethyl 6-chloro-2-phenyl-4-quinolone-3-carboxylate (VII-16)

Following the procedure of method A for preparing compound VII-1, product VII-16 (0.85 g, 26%) was obtained; colorless needles; mp 235.5–237.3° C. (dec.); $^1$H NMR (DMSO-$d_6$) δ 0.89 (3H, t, J=7.0 Hz, CH$_3$), 3.96 (2H, q, J=7.0 Hz, CH$_2$), 7.57 (5H, m, H-2', H-3', H-4', H-5', H-6') 7.69–7.80 (2H, m, H-7, H-8), 8.05 (1H, d, J=2.0 Hz, H-5), 12.26 (1H, s NH),; IR (KBr) v 1717, 1623 (—C=O) cm$^{-1}$; MS (M$^+$) m/z 327. Anal. calcd C, 65.96; H, 4.31; N, 4.27. Found, C, 66.01; H, 4.29; N, 4.24.

Ethyl 2'-chloro-6-fluoro-2-phenyl-4-quinolone-3-carboxylate (VII-18)

Following the procedure of method A for preparing compound VII-1, product VII-18 (1.17 g, 34%) was obtained; colorless needles; mp 215.3–216.8° C.;$^1$H NMR (DMSO-$d_6$) δ 0.80 (3H, t, J=7.0 Hz, CH$_3$), 3.87 (2H, q, J=7.0 Hz, CH$_2$), 7.48–7.69 (6H, m, H-7, H-8, H-3', H-4', H-5', H-6'), 7.80 (1H, dd, J=8.9, 2.5 Hz, H-5), 12.46 (1H, s, NH); IR (KBr) v 3219 (—NH), 1722 (—C=O) cm$^{-1}$; MS (M$^+$) m/z 345. Anal. calcd C, 62.53; H, 3.79; N, 4.05. Found, C, 62.54; H, 3.78; N, 4.07.

Ethyl 6-fluoro-2'-methoxy-2-phenyl-4-quinolone-3-carboxylate (VII-19)

Following the procedure of method A for preparing compound VII-1, product VII-19 (0.92 g, 27%) was obtained; colorless needles; mp 200.8–202.1° C.; $^1$H NMR (DMSO-$d_6$) δ 0.84 (3H, t, J=7.0 Hz, CH$_3$), 3.76 (3H, s, OCH$_3$), 3.88 (2H, q, J=7.0 Hz, CH$_2$), 7.07 (1H, dd, J=7.4, 7.4 Hz, H-5'), 7.18 (1H, d, J=8.4 Hz, H-3'), 7.33 (1H, d, J=7.4 Hz, H-6'), 7.52 (1H, dd, J=8.4, 7.4 Hz, H-4'), 7.60–7.70 (2H, m, H-7, H-8), 7.77 (1H, dd, J=9.3, 2.6 Hz, H-5), 12.20 (1H, s, NH); IR (KBr) v 1720 (—C=O) cm$^{-1}$; MS (M$^+$) m/z 341. Anal. calcd C, 66.86; H, 4.72; N, 4.10. Found, C, 66.87; H, 4.73; N, 4.08.

Ethyl 2'-fluoro-6-methoxy-2-phenyl-4-quinolone-3-carboxylate (VII-20)

Following the procedure of method A for preparing compound VII-1, product VII-20 (1.30 g, 38%) was obtained; colorless needles; mp 227.7–229.4° C.; $^1$H NMR (DMSO-$d_6$) δ 0.85 (3H, t, J=7.0 Hz, CH$_3$), 3.85 (3H, s, OCH$_3$), 3.91 (2H, q, J=7.0 Hz, CH$_2$), 7.32–7.67 (7H, m, H-5, H-7, H-8, H-3', H-4', H-5', H-6'), 12.28 (1H, s, NH); IR (KBr) v 1719, 1622 (—C═O) cm$^{-1}$; MS (M$^+$) m/z 341. Anal. calcd C, 66.86; H, 4.72; N, 4.10. Found, C, 66.85; H, 4.73; N, 4.12.

Ethyl 4'-fluoro-6-methoxy-2-phenyl-4-quinolone-3-carboxylate (VII-22)

Following the procedure of method A for preparing compound VII-1, product VII-22 (1.53 g, 45%) was obtained; colorless needles; mp 202.3–204.5° C.; $^1$H NMR (DMSO-$d_6$) δ 0.93 (3H, t, J=7.0 Hz, CH$_3$), 3.84 (3H, s, OCH$_3$), 3.98 (2H, q, J=7.0 Hz, CH$_2$), 7.32–7.44 (3H, m, H-7, H-3', H-5'), 7.52 (1H, d, J=2.8 Hz, H-5), 7.59–7.67 (3H, m, H-8, H-2', H-6'), 12.08 (1H, s, NH); IR (KBr) v 1713, 1608 (—C═O) cm$^{-1}$; MS (M$^+$) m/z 341. Anal. calcd C, 66.86; H, 4.72; N, 4.10. Found, C, 66.88; H, 4.71; N, 4.11.

Ethyl 6,7-methylenedioxy-2-phenyl-4-quinolone-3-carboxylate (VII-23)

Following the procedure of method A for preparing compound VII-1, product VII-23 (1.38 g, 41%) was obtained; colorless needles; mp 237.2–238.8° C. (dec.); $^1$H NMR (DMSO-$d_6$) δ 0.90 (3H, t, J.=7.0 Hz, CH$_3$), 3.94 (2H, q, J=7.0 Hz, CH$_2$), 6.17 (2H, s, OCH$_2$O), 7.09 (1H, s, H-8), 7.40 (1H, s, H-5), 7.54 (5H, m, H-2', H-3', H-4', H-5', H-6'), 11.93 (1H, s, NH); IR (KBr) v 1715, 1634 (—C═O) cm$^{-1}$; MS (M$^+$) m/z 337. Anal. calcd C, 67.65; H, 4.48; N, 4.15. Found, C, 67.62; H, 4.50; N, 4.12.

3'-Chloro-6-fluoro-2-phenyl-4-quinolone-3-carboxylic acid (IX-1)

Compound VII-1 (1.04 g, 3 mmol) was stirred in 10% NaOH (100 ml) until completely dissolved (ca 1 h). The solution was cooled to 5°±2° C. and acidified with dil. HCl. The resulted precipitates were collected by filtration, washed with water, recrystallozed from EtOH to afford the desired carboxylic acid; amorphous colorless (0.86 g, 90%); mp 263° C.; $^1$H NMR (DMSO-$d_6$) δ 7.46 (1H, d, J=7.4 Hz, H-6'), 7.52 (1H, d, J=7.5 Hz, H-5'), 7.58–7.61 (2H, m, H-2', H-4'), 7.76 (1H, ddd, J=2.8, 8.8 Hz, H-7), 7.85 (1H, dd, J=9.0, 4.6 Hz, H-8), 7.90 (1H, dd, J=9.3, 2.8 Hz, H-5); IR (KBr) v 3454 (—NH), 1631 (—C═O) cm$^{-1}$; MS (M$^+$) m/z 317.7. Anal. calcd C, 60.49; H, 2.86; N, 4.41. Found, C, 60.59; H, 2.85; N, 4.39.

3',6-Difluoro-2-phenyl-4-quinolone-3-carboxylic acid (IX-2): obtained from compound VII-2 (0.99 g, 3 mmol) as described in the preparation of compound IX-1; amorphous colorless (0.78 g, 86%); mp 272° C. (dec); $^1$H NMR (DMSO-$d_6$) δ 7.27–7.33 (3H, m, H-2', H-4', H-6'), 7.46–7.51 (1H, m, H-5'), 7.70 (1H, ddd, J=3.0, 8.8, 8.7 Hz, H-7), 7.84 (1H, dd, J=9.0, 4.7 Hz, H-8), 7.91 (1H, dd, J=9.3, 3.0 Hz, H-5); IR (KBr) v 1677, 1620 (—C═O) cm$^{-1}$; MS (M$^+$) m/z 301.3. Anal. calcd C, 63.79; H, 3.01; N, 4.65. Found, C, 63.94; H, 3.01; N, 4.67.

6-Fluoro-3'-methoxy-2-phenyl-4-quinolone-3-carboxylic acid (IX-3): obtained from compound VII-3 (1.02 g, 3 mmol) as described in the preparation of compound IX-1; amorphous colorless (0.84 g, 89%); mp 231° C.; $^1$H NMR (DMSO-$d_6$) δ 3.97 (3H, s, OCH$_3$), 7.06–7.11 (3H, m, H-2', H-4', H-6'), 7.42 (1H, m, H-5'), 7.77 (1H, dd, J=2.9, 8.6 Hz, H-7), 7.86–7.93 (2H, m, H-5, H-8); IR (KBr) v 3450 (—NH), 1679, 1617 (—C═O) cm$^{-1}$; MS (M$^+$) m/z 313.3. Anal. calcd C, 65.18; H, 3.86; N, 4.47. Found, C, 65.01; H, 3.86; N, 4.45.

6-Fluoro-2-phenyl-4-quinolone-3-carboxylic acid (IX-4): obtained from compound VII-4 (0.93 g, 3 mmol) as described in the preparation of compound IX-1; amorphous colorless (0.76 g, 89%); mp 297° C.; $^1$H NMR (DMSO-$d_6$) δ 7.52 (5H, m, H-7, H-8, H-3', H-4', H-5'), 7.74–7.95 (3H, m, H-5, H-2', H-6'), 13.08 (1H, br, NH), 15.50 (1H, br, OH); IR (KBr) v 1674 (—C═O) cm$^{-1}$; MS (M$^+$) m/z 283. Anal. calcd C, 67.84; H, 3.56; N, 4.94. Found, C, 67.60; H, 3.57; N, 4.92.

3'-Fluoro-6-chloro-2-phenyl-4-quinolone-3-carboxylic acid (IX-5): obtained from compound VII-5 (1.73 g, 3 mmol) as described in the preparation of compound IX-1; amorphous colorless (1.40 g, 88%); mp>300° C.; $^1$H NMR (DMSO-$d_6$) δ 7.37–7.58 (4H, m, H-2', H-4', H-5', H-6'), 7.72–7.76 (2H, mH-7, H-8), 8.05 (1H, d, J=2.2 Hz, H-5), 12.38 (1H, br, NH); IR (KBr) v 3430 (—NH), 1687, 1635 (—C═O) cm$^{-1}$; MS (M$^+$) m/z 317.7. Anal. calcd C, 60.49; H, 2.86; N, 4.41. Found, C, 60.24; H, 2.86; N, 4.42.

3',6-Dichloro-2-phenyl-4-quinolone-3-carboxylic acid (IX-6): obtained from compound VII-6 (1.81 g, 3 mmol) as described in the preparation of compound IX-1; amorphous colorless (1.52 g, 91%); mp 260° C.(dec); $^1$H NMR (DMSO-$d_6$) δ 7.47 (1H, d, J=7.58 Hz, H-4'), 7.53 (1H, dd, J=7.9, 7.9 Hz, H-5'), 7.59–7.63 (2H, m, H-2', H-6'), 7.80 (1H, d, J=8.9 Hz, H-8), 7.89 (1H, dd, J=8.9, 2.6 Hz, H-7), 8.20 (1H, d, J=2.4 Hz, H-5); IR (KBr) v 3452 (—NH), 1680, 1635 (—C═O) cm$^{-1}$; MS (M$^+$) m/z 334.2. Anal. calcd C, 57.51; H, 2.72; N, 4.19. Found, C, 57.70; H, 2.70; N, 4.20.

3'-Methoxy-6-chloro-2-phenyl-4-quinolone-3-carboxylic acid (IX-7): obtained from compound VII-7 (1.79 g, 3 mmol) as described in the preparation of compound IX-1; amorphous colorless (1.46 g, 89%); mp 243° C. (dec); $^1$H NMR (DMSO-$d_6$) δ 7.05 (3H, m, H-2', H-4', H-6'), 7.40 (1H, dd, J=8.3 Hz, H-5'), 7.80 (1H, d, J=8.9 Hz, H-8), 7.91 (1H, dd, J=8.8, 2.4 Hz, H-7), 8.19 (1H, d, J=2.4 Hz, H-5), 13.01 (1H, br-s, NH), 15.37 (1H, br-s, OH); IR (KBr) v 3450 (—NH), 1675 (—C═O) cm$^{-1}$; MS (M$^+$) m/z 329.7. Anal. calcd C, 61.92; H, 3.67; N, 4.25. Found, C, 62.11; H, 3.66; N, 4.26.

3'-Fluoro-6-methoxy-2-phenyl-4-quinolone-3-carboxylic acid (IX-8): obtained from compound VII-8 (1.71 g, 3 mmol) as described in the preparation of compound IX-1; amorphous colorless (1.46 g, 93%); mp 268° C. (dec); $^1$H NMR (DMSO-$d_6$) δ 3.76 (3H, s, OCH$_3$), 7.07–7.12 (2H, m, H-2', H-4'), 7.17 (1H, d, J=7.9 Hz, H-6'), 7.28 (1H, dd, J=2.9, 9.2 Hz, H-7), 7.31–7.42 (1H, m, H-5'), 7.56 (1H, d, J=2.9 Hz, H-5), 7.65 (1H, d, J=9.0 Hz, H-8); IR (KBr) v 1680, 1625 (—C═O) cm$^{-1}$; MS (M$^+$) m/z 313.3. Anal. calcd C, 65.18; H, 3.86; N, 4.47. Found, C, 65.38; H, 3.87; N, 4.49.

3'-Chloro-6-methoxy-2-phenyl-4-quinolone-3-carboxylic acid (IX-9): obtained from compound VII-9 (1.79 g, 3 mmol) as described in the preparation of compound IX-1; amorphous colorless (1.48 g, 90%); mp 223° C. (dec); $^1$H NMR (DMSO-$d_6$) δ 3.91 (3H, s, OCH$_3$), 7.43–7.66 (6H, m, H-5, H-7, H-2', H-4', H-5', H-6'), 7.77 (1H, d, J=9.1 Hz, H-8), 13.15 (1H, br-s, NH); IR (KBr) v 3444 (—NH), 1679, 1624 (—C═O) cm$^{-1}$; MS (M$^+$) m/z 329.7. Anal. calcd C, 61.92; H, 3.67; N, 4.25. Found, C, 62.09; H, 3.67; N, 4.24.

3',6-Dimethoxy-2-phenyl-4-quinolone-3-carboxylic acid (IX-10): obtained from compound VII-10 (1.63 g, 3 mmol) as described in the preparation of compound IX-1; amorphous colorless (1.50 g, 92%); mp>300° C.; $^1$H NMR (DMSO-$d_6$) δ 3.90 (3H, s, OCH$_3$), 7.03–7.08 (3H, m, H-4', H-5', H-6'), 7.37–7.49 (2H, m, H-7, H-2'), 7.59 (1H, m, H-5), 7.75 (1H, d, J=9.0 Hz, H-8), 13.03 (1H, br, NH), 16.02 (1H, br, OH); IR (KBr) v 3455 (—NH), 1677, 1624 (—C═O) cm$^{-1}$; MS (M$^+$) m/z 325.3. Anal. calcd C, 66.46; H, 4.65; N, 4.31. Found, C, 66.67; H, 4.67; N, 4.29.

6-Methoxy-2-phenyl-4-quinolone-3-carboxylic acid (IX-11): obtained from compound VII-11 (1.62 g, 3 mmol) as described in the preparation of compound IX-1; amorphous colorless (1.62 g, 85%); mp>300° C.; $^1$H NMR (DMSO-$d_6$) δ 3.91 (3H, s, OCH$_3$), 7.49–7.50 (5H, m, H-2', H-3', H-4', H-5', H-6'), 7.54 (1H, d, J=2.9 Hz, H-7), 7.65 (1H, d, J=2.8 Hz, H-5), 7.79 (1H, d, J=9.1 Hz, H-8); IR (KBr) v 3450 (—NH), 1672, 1619 (—C=O) cm$^{-1}$; MS (M$^+$) m/z 295.3. Anal. calcd C, 69.15; H, 4.44; N, 4.74. Found, C, 69.37; H, 4.46; N, 4.75.

6-Chloro-2'-fluoro-2-phenyl-4-quinolone-3-carboxylic acid (XI-12): obtained from compound VII-13 (0.63 g, 2 mmol) as described in the preparation of compound IX-1; amorphous colorless (0.58 g, 92%); mp 227.6–229.1° C.; $^1$H NMR (DMSO-$d_6$) δ 7.26–7.37 (2H, m, H-3', H-5'), 7.50–7.61 (2H, m, H-4', H-6'), 7.80 (1H, d, J=8.9 Hz, H-8), 7.89 (1H, dd, J=8.9, 2.3 Hz, H-7), 8.23 (1H, d, J=2.3 Hz, H-5), 15.96 (1H, s, OH); IR (KBr) v 3452 (—NH), 1682, 1634 (—C=O) cm$^{-1}$; MS (M$^+$) m/z 317. Anal. calcd C, 60.49; H, 2.86; N, 4.41. Found, C, 60.51; H, 2.85; N, 4.39.

2',6-Dichloro-2-phenyl-4-quinolone-3-carboxylic acid (IX-13): obtained from compound VII-14 (0.67 g, 2 mmol) as described in the preparation of compound IX-1; amorphous colorless (0.59 g, 89%); mp 242.8–244.9° C.; $^1$H NMR (DMSO-$d_6$) δ 7.43–7.63 (4H, m, H-3', H-4', H-5', H-6'), 7.81 (1H, d, J=8.9 Hz, H-8), 7.93 (1H, dd, J=8.9, 2.4 Hz, H-7), 8.25 (1H, d, J=2.4 Hz, H-5), 13.57 (1H, s, NH), 15.74 (1H, s, OH); IR (KBr) v 3466 (—NH), 1690, 1632 (—C=O) cm$^{-1}$; MS (M$^+$) m/z 333. Anal. calcd C, 57.51; H, 2.71; N, 4.19. Found, C, 57.48; H, 2.72; N, 4.20.

6-Chloro-2'-methoxy-2-phenyl-4-quinolone-3-carboxylic acid (IX-14): obtained from compound VII-15 (0.66 g, 2 mmol) as described in the preparation of compound IX-1; amorphous colorless (0.59 g, 90%); mp 221.1–223.6° C.; $^1$H NMR (DMSO-$d_6$) δ 3.72 (3H, s, OCH$_3$), 7.07 (1H, dd, J=7.4, 7.4 Hz, H-5'), 7.15 (1H, d, J=8.3 Hz, H-3'), 7.34 (1H, dd, J=7.4, 1.4 Hz, H-6'), 7.51 (1H, ddd, J=8.3, 7.4, 1.4 Hz, H-4'), 7.80 (1H, d, J=8.9 Hz, H-8), 7.92 (1H, dd, J=8.9, 2.3 Hz, H-7), 8.23 (1H, d, J=2.3 Hz, H-5), 13.26 (1H, s, NH), 15.57 (1H, s, OH); IR (KBr) v 1680, 1634 (—C=O) cm$^{-1}$; MS (M$^+$) m/z 329. Anal. calcd C, 61.92; H, 3.67; N, 4.25. Found, C, H, 3.66; N, 4.23.

6-Chloro-2-phenyl-4-quinolone-3-carboxylic acid (IX-15): obtained from compound VII-16 (0.30 g, 1 mmol) as described in the preparation of compound IX-1; amorphous colorless (0.28 g, 93%); mp 254.2–255.6° C. (dec.); $^1$H NMR (DMSO-$d_6$) δ 7.53 (5H, m, H-2', H-3', H-4', H-5', H-6'), 7.81 (1H, d, J=8.9 Hz, H-8), 7.90 (1H, dd, J=8.9, 2.0 Hz, H-7), 8.19 (1H, d, J=2.0 Hz, H-5), 13.05 (1H, s, NH), 15.28 (1H, s, OH); IR (KBr) v 1684, 1634 (—C=O) cm$^{-1}$; MS (M$^+$) m/z 299. Anal. calcd C, 64.12; H, 3.36; N, 4.67. Found, C, 64.15; H, 3.36; N, 4.66.

2',6-Difluoro-2-phenyl-4-quinolone-3-carboxylic acid (IX-16): obtained from compound VII-17 (0.30 g, 1 mmol) as described in the preparation of compound IX-1; amorphous colorless (0.26 g, 87%); mp 233.4–234.7° C. (dec.); $^1$H NMR (DMSO-$d_6$) δ 7.31–7.41 (2H, m, H-3', H-5'), 7.55–7.66 (2H, m, H-4', H-6'), 7.77–7.87 (2H, m, H-7, H-8), 7.95 (1H, dd, J=9.0, 2.5 Hz, H-5), 13.50 (1H, s, NH), 15.76 (1H, s, OH); IR (KBr) v 3454 (—NH), 1672, 1616 (—C=O) cm$^{-1}$; MS (M$^+$) m/z 301. Anal. calcd C, 63.79; H, 3.01; N, 4.65. Found, C, 63.80; H, 3.00; N, 4.66.

2'-Chloro-6-fluoro-2-phenyl-4-quinolone-3-carboxylic acid (IX-17): obtained from compound VII-18 (0.63 g, 2 mmol) as described in the preparation of compound IX-1; amorphous colorless (0.56 g, 88%); mp 269.1–271.0° C.; $^1$H NMR (DMSO-$d_6$) δ 7.45–7.63 (4H, m, H-3', H-4', H-5', H-6'), 7.78–7.92 (2H, m, H-7, H-8), 8.00 (1H, dd, J=8.7, 2.3 Hz, H-5), 13.53 (1H, s, NH), 15.75 (1H, s, OH),; IR (KBr) v 1684, 1612 (—C=O) cm$^{-1}$; MS (M$^+$) m/z 317. Anal. calcd C, 60.49; H, 2.86; N, 4.41. Found, C, 60.52; H, 2.83; N, 4.38.

6-Fluoro-2'-methoxy-2-phenyl-4-quinolone-3-carboxylic acid (IX-18): obtained from compound VII-19 (0.31 g, 1 mmol) as described in the preparation of compound IX-1; amorphous colorless (0.28 g, 90%); mp 254.2–255.8° C.; $^1$H NMR (DMSO-$d_6$) δ 3.70 (3H, s, OCH$_3$), 7.03–7.15 (2H, m, H-3', H-5'), 7.32 (1H, dd, J=7.4, 1.4 Hz, H-6'), 7.49 (1H, ddd, J=8.4, 7.4, 1.4 Hz, H-4'), 7.79–7.86 (2H, m, H-7, H-8), 7.96 (1H, dd, J=9.0, 2.6 Hz), 13.57 (1H, s, NH), 15.74 (1H, s, OH); IR (KBr) v 3470 (—NH), 1676, 1611 (—C=O) cm$^{-1}$; MS (M$^+$) m/z 313. Anal. calcd C, 65.18; H, 3.86; N, 4.47. Found, C, 65.20; H, 3.88; N, 4.46.

2'-Fluoro-6-methoxy-2-phenyl-4-quinolone-3-carboxylic acid (IX-19): obtained from compound VII-20 (0.63 g, 2 mmol) as described in the preparation of compound IX-1; amorphous colorless (0.56 g, 89%); mp 249.1–251.3° C. (dec.); $^1$H NMR (DMSO-$d_6$) δ 3.92 (3H, s, OCH$_3$), 7.29–7.39 (2H, m, H-3', H-5'), 7.51–7.60 (3H, m, H-7, H-4', H-6'), 7.67 (1H, d, J=2.8 Hz, H-5), 7.78 (1H, d, J=9.1 Hz, H-8), 13.39 (1H, s, NH); IR (KBr) v 1674, 1616 (—C=O) cm$^{-1}$; MS (M$^+$) m/z 313. Anal. calcd C, 65.18; H, 3.86; N, 4.47. Found, C, 65.21; H, 3.83; N, 4.46.

2'-Chloro-6-methoxy-2-phenyl-4-quinolone-3-carboxylic acid (IX-20): obtained from compound VII-21 (0.99 g, 3 mmol) as described in the preparation of compound IX-1; amorphous colorless (0.91 g, 92%); mp 264.2–267.1° C.; $^1$H NMR (DMSO-$d_6$) δ 3.91 (3H, s, OCH$_3$), 7.44–7.62 (5H, m, H-7, H-3', H-4', H-5', H-6'), 7.66 (1H, d, J=2.6 Hz, H-5), 7.76 (1H, d, J=9.0 Hz, H-8), 13.42 (1H, s, NH); IR (KBr) v 3462 (—NH), 1678, 1616 (—C=O) cm$^{-1}$; MS (M$^+$) m/z 329. Anal. calcd C, 61.92; H, 3.67; N, 4.25. Found, C, 61.93; H, 3.65; N, 4.27.

4'-Fluoro-6-methoxy-2-phenyl-4-quinolone-3-carboxylic acid (IX-21): obtained from compound VII-22 (1.25 g, 4 mmol) as described in the preparation of compound IX-1; amorphous colorless (1.14 g, 91%); mp 273.6–275.3° C.; $^1$H NMR (DMSO-$d_6$) δ 3.88 (3H, s, OCH$_3$), 7.34 (2H, dd, J=8.6, 8.6 Hz, H-3', H-5'), 7.47 (1H, dd, J=9.0, 2.6 Hz, H-7), 7.54–7.61 (3H, m, H-5, H-2', H-6'), 7.73 (1H, d, J=9.0 Hz, H-8), 13.04 (1H, s, NH); IR (KBr) v 3466 (—NH), 1680, 1622 (—C=O) cm$^{-1}$; MS (M$^+$) m/z 313. Anal. calcd C, 65.18; H, 3.86; N, 4.47. Found, C, 65.20; H, 3.85; N, 4.47.

6,7-Methylenedioxy-2-phenyl-4-quinolone-3-carboxylic acid (IX-22): obtained from compound VII-23 (0.93 g, 3 mmol) as described in the preparation of compound IX-1; amorphous colorless (0.86 g, 93%); mp 267.5–269.2° C. (dec.); $^1$H NMR (DMSO-$d_6$) δ 6.25 (2H, s, OCH$_2$O), 7.20 (1H, s, H-8), 7.49 (5H, m, H-2', H-3', H-4', H-5', H-6'), 7.56 (1H, s, H-5), 12.90 (1H, s, NH); IR (KBr) v 3454 (—NH), 1684, 1645 (—C=O) cm$^{-1}$; MS (M$^+$) m/z 309. Anal. calcd C, 66.02; H, 3.58; N, 4.53. Found, C, 66.05; H, 3.57; N, 4.52.

3'-Chloro-6-fluoro-2-phenyl-4-quinolone-3-carboxylic acid tromethamine salt (X-1)

A solution of compound IX-1 (0.32 g, 1 mmol) in butyl chloride (20 ml) was treated with a methanolic solution (10 ml) of tromethamine (0.12 g, 1 mmol) and an additional 20 ml of butyl chloride to yield 0.41 g (93%) of a white solid precipitate which was dried overnight at 50° C. under reduced pressure; mp 241° C. (dec); $^1$H NMR (DMSO-$d_6$) δ 3.46 (CH$_2$OH), 5.16 (3H, br, OH), 7.26–7.33 (4H, m, H-2', H-4', H-5', H-6'), 7.49 (1H, ddd, J=8.7, 3.0 Hz, H-7), 7.74 (1H, dd, J=9.2, 5.2 Hz, H-8), 7.79 (1H, dd, J=8.8, 3.1 Hz, H-5); IR (KBr) v 3432, 3228 cm$^{-1}$ (—NH); MS (M$^+$) m/z 438.8. Anal. C, H, N.

3',6-Difluoro-2-phenyl-4-quinolone-3-carboxylic acid tromethamine salt (X-2): obtained from compound IX-2 (0.30 g, 1 mmol) according to the procedure described in the preparation of compound X-1; amorphous colorless (0.40 g, 94%); mp>300° C.; $^1$H NMR (DMSO-d$_6$) δ 3.49 (CH$_2$OH), 5.08 (br,OH), 7.04–7.15 (3H, m, H-2', H-4', H-6'), 7.31 (1H, m, H-5'), 7.48 (1H, ddd, J=9.0, 3.0 Hz, H-7), 7.69–7.82 (2H, m, H-5, H-8); IR (KBr) v 3391 cm$^{-1}$ (—NH); MS (M$^+$) m/z 422.4. Anal. C, H, N.

3'-Methoxy-6-fluoro-2-phenyl-4-quinolone-3-carboxylic acid tromethamine salt (X-3): obtained from compound IX-3 (0.31 g, 1 mmol) according to the procedure described in the preparation of compound X-1; amorphous colorless (0.40 g, 93%); mp 222° C.; $^1$H NMR (DMSO-d$_6$) δ 3.50 (CH$_2$OH), 3.75 (3H, s, OCH$_3$), 5.11 (3H, br, OH), 6.84–6.89 (3H, m, H-2', H-4', H-6'), 7.20 (1H, m, H-5'), 7.48 (1H, ddd, J=9.2, 2.9 Hz, H-7), 7.67–7.80 (2H, m, H-5, H-8); IR (KBr) v 3384 cm$^{-1}$; MS (M$^+$) m/z 434.4. Anal. C, H, N.

6-Fluoro-2-phenyl-4-quinolone-3-carboxylic acid tromethamine salt (X-4): obtained from compound IX-4 (0.28 g, 1 mmol) and tromethamine (0.12 g, 1 mmol) according to the procedure described in the preparation of compound X-1; amorphous colorless (0.36 g, 89%); $^1$H NMR (DMSO-d$_6$) δ 3.71 (3×CH$_2$OH), 5.12 (3H, br, 3×OH), 7.26–7.36 (5H, m, H-7, H-8, H-3', H-4', H-5'), 7.58–7.91 (3H, m, H-5, H-2', H-6'); ▮ mp>300° C.; IR (KBr) v 3378 cm$^{-1}$; MS (M$^+$) m/z 404.4. Anal. C, H, N.

3'-Fluoro-6-chloro-2-phenyl-4-quinolone-3-carboxylic acid tromethamine salt (X-5): obtained from compound IX-5 (0.32 g, 1 mmol) according to the procedure described in the preparation of compound X-1; amorphous colorless (0.41 g, 93%); mp 262° C. (dec); $^1$H NMR (DMSO-d$_6$) δ 3.60 (3× CH$_2$OH), 5.15 (3H, br, 3×OH), 7.06–7.15 (3H, m, H-4', H-5', H-6'), 7.31 (1H, dd, J=7.3 Hz, H-2'), 7.59 (1H, dd, J=9.0, 2.4 Hz, H-7), 7.68 (1H, d, J=8.9 Hz, H-8), 8.11 (1H, d, J=2.3 Hz, H-5); IR (KBr) v 3375 cm$^{-1}$ (—NH); MS (M$^+$) m/z 438.8. Anal. C, H, N.

3',6-Dichloro-2-phenyl-4-quinolone-3-carboxylic acid tromethamine salt (X-6): obtained from compound IX-6 (0.33 g, 1 mmol) according to the procedure described in the preparation of compound X-1; amorphous colorless (0.43 g, 94%); mp 272° C. (dec); $^1$H NMR (DMSO-d$_6$) δ3.60 (3× CH$_2$OH), 5.15 (3H, br, 3×OH), 7.25–7.33 (4H, m, H-2', H-4', H-5', H-6'), 7.58 (1H, dd, J=8.8, 2.4 Hz, H-7), 7.69 (1H, d, J=8.8 Hz, H-8), 8.12 (1H, d, J=2.4 Hz, H-5); IR (KBr) v 3228 cm$^{-1}$ (—NH); MS (M$^+$) m/z 455.3. Anal. C, H, N.

3'-Methoxy-6-chloro-2-phenyl-4-quinolone-3-carboxylic acid tromethamine salt (X-7): obtained from compound IX-7 (0.33 g, 1 mmol) according to the procedure described in the preparation of compound X-1; amorphous colorless (4.1 g, 92%); mp 261° C. (dec); $^1$H NMR (DMSO-d$_6$) δ 3.75 (3H, s, OCH$_3$), 5.10 (3H, br, 3×OH), 6.82–6.90 (3H, m, H-2', H-4', H-6'), 7.16–7.20 (1H, m, H-5'), 7.57 (1H, dd, J=8.8, 2.4 Hz, H-7), 7.67 (1H, d, J=8.8 Hz, H-8), 8.11 (1H, d, J=2.3 Hz, H-5); IR (KBr) v 3379 cm$^{-1}$ (—NH); MS (M$^+$) m/z 450.9. Anal. C, H, N.

3'-Fluoro-6-methoxy-2-phenyl-4-quinolone-3-carboxylic acid tromethamine salt (X-8): obtained from compound IX-8 (0.31 g, 1 mmol) according to the procedure described in the preparation of compound X-1; amorphous colorless (0.41 g, 95%); mp 268–269° C.; $^1$H NMR (DMSO-d$_6$) δ 3.81 (3× CH$_2$OH), 3.86 (3H, s, OCH$_3$), 4.78 (3H, br, 3×OH), 7.08–7.34 (5H, m, H-2', H-3', H-4', H-5'), 7.54 (1H, d, J=2.8 Hz, H-5), 7.63 (1H, d, J=9.8 Hz, H-8); IR (KBr) v 3256 cm$^{-1}$ (br, —NH); MS (M$^+$) m/z 434.4. Anal. C, H, N.

3'-Chloro-6-methoxy-2-phenyl-4-quinolone-3-carboxylic acid tromethamine salt (X-9): obtained from compound IX-9 (0.33 g, 1 mmol) according to the procedure s described in the preparation of compound X-1; amorphous colorless (0.42 g, 94%); mp 144° C.; $^1$H NMR (DMSO-d$_6$) δ 3.85 (3×CH$_2$OH), 3.87 (3H, s, OCH$_3$), 4.81 (3H, br, 3×OH), 7.27–7.37 (5H, m, H-2', H-4', H-5', H-6', H-7), 7.56 (1H, d, J=2.6 Hz, H-5), 7.66 (1H, d, J=9.1 Hz, H-8); IR (KBr) v 3341 cm$^{-1}$ (—NH), 1621 cm$^{-1}$ (—C=O); MS (M$^+$) m/z 450.9. Anal. C, H, N.

3',6-Dimethoxy-2-phenyl-4-quinolone-3-carboxylic acid tromethamine salt (X-10): obtained from compound IX-10 (0.33 g, 1 mmol) according to the procedure described in the preparation of compound X-1; amorphous colorless (0.42 g, 93%); mp 225° C.; $^1$H NMR (DMSO-d$_6$) δ 3.74 (3×CH$_2$OH), 4.85 (3H, br, 3×OH), 6.83–6.91 (3H, m, H-4', H-5', H-6'), 7.17–7.29 (2H, m, H-7, H-2'), 7.52 (1H, m, H-5), 7.63 (1H, d, J=9.0 Hz, H-8); IR (KBr) v 3252 cm$^{-1}$ (—NH); MS (M$^+$) m/z 446.5. Anal. C, H, N.

6-Methoxy-2-phenyl-4-quinolone-3-carboxylic acid tromethamine salt (X-11): obtained from compound IX-11 (0.30 g, 1 mmol) and tromethamine (0.12 g, 1 mmol) according to the procedure described in the preparation of compound X-1; amorphous colorless (0.39 g, 93%); mp>300° C.; $^1$H NMR (DMSO-d$_6$) δ 3.37 (3×CH$_2$OH), 3.85 (3H, s, OCH$_3$), 4.88 (3H, br, 3×OH), 7.22–7.33 (6H, m, H-2', H-3', H-4', H-5', H-6', H-7), 7.52 (1H, d, J=2.9 Hz, H-5), 7.61 (1H, d, J=9.0 Hz, H-8); IR (KBr) v 3382 cm$^{-1}$ (—NH); MS (M$^+$) m/z 416.4. Anal. C, H, N.

Preliminary Cytotoxicity Assay

Compounds were assayed for in vitro cytotoxicity in a panel of human tumor cell lines at the School of Pharmacy, University of North Carolina at Chapel Hill, according to procedures described previously [Lee, K. H., Lin, Y. M., Wu, T. S., Zhang, D. C., Yamagishi, T., Hayashi, T., Hall, I. H., Chang, J. J., Wu, R. Y., Yang, T. H. The cytotoxic principles of *Prunella vulgaris, Psychotria serpens*, and *Hyptis capitata*: Ursolic acid and related derivatives. *Planta Med*. 1988, 54, 308–11; Boyd, M. R. Status of the National Cancer Institute preclinical antitumor drug discovery screen: implications for selection of new agents for clinical trial. Devita, V. T., Jr. Hellman, S., Rosenberg, S. A., Eds, J. B. Cancer: Principles and Practice of Oncology Update, 1989, 3: pp1–12, Lippincoft: Philadephia; Monks, A., Scudiero, D., Skehan, P., Shoemaker, R., Paull, K., Vistica, D., Hose, C., Langley, J., Cronise, P., Vaigro-Wolff, A., Gray-Goodrich, M., Campbell, H., Mayo, J., Boyd, M. Feasibility of a high-flux anticancer drug screen using a diverse panel of cultured human tumor cell lines. *J. Natl. Cancer Inst*. 1991, 83, 757–66.] The cell lines included human ovarian cancer (1A9), ileocecal carcinoma (HCT-8), lung carcinoma (A-549), glioblastoma (U-87-MG), bone (HOS), epidermoid carcinoma of the naynx (KB), P-gp-expressing epidermoid carcinoma of the nasopharynx (KB-VIN), and melanoma (SKMEL-2) cell line. The cytotoxic effects of each compound were obtained as EC$_{50}$ values, which represent the molar drug concentrations required to cause 50% inhibition.

Evaluation Against Human Cancer Cell Line Panel Cell Lines.

Compound IX-8 was evaluated growth inhibition activities against a panel of 39 human cancer cell lines including Human breast cancer MDA-MB-231 and the following human cancer cell lines were generously distributed by the National Cancer Institute (Frederick, Md.): lung cancer, NCI-H23, NCI-H226, NCI-H522, NCI-H460, A-549, DMS273 and DMS114; colon cancer, HGC-2998, KM-12, HT-29, HCT-15, and HCT-116; ovarian cancer, OVCAR-3, OVCAR-4, OVCAR-5, OVCAR-8, and SKOV-3; breast cancer, MCF-7; renal cancer, RXF-631L and ACHN; melanoma, LOX-IMVI; brain tumor, U251, SF-295, SF-539, SF-268, SNB-75, and SNB-78, and prostate cancer, DU-145 and PC-3. Human stomach cancer, MKN-1, MKN-7, MKN-28, MKN-45, MKN-74, and St-4, and human breast cancer BSY-1, HBC-4, and HBC-5 described elsewhere [Stinson, S. F., Alley, M. C., Kopp, W. C., Fiebig, H. H., Mullendore, L. A., Pittman, A. F., Kenney, S., Keller, J., Boyd, M. R. Morphological and immunocytochemical characteristics of human tumor cell lines for use in a disease-oriented anticancer drug screen. *Anticancer Res.* 1992, 12, 1035–53; Satoh, A., Takayama, E., Kojima, K., Ogawa, H., Yamori, T., Sato, S., Kawaguchi, T., Tsuruo, T., Yoshimoto, K., Kine, T., Matsumoto, I. Expression of carbohydrate-binding protein p33/41 in human tumor cell lines. *J. Biochem.* 1996, 119, 346–53; Motoyama, T., Hojo, H., Watanabe, H. Comparison of seven cell lines derived from human gastric carcinomas. *Acta. Pathol. Jpn.* 1986, 36, 65–83.] The evaluation was according to the method of the National Cancer Institute with modification [Lee, K. H., Lin, Y. M., Wu, T. S., Zhang, D. C., Yamagishi, T., Hayashi, T., Hall, I. H., Chang, J. J., Wu, R. Y., Yang, T. H. The cytotoxic principles of *Prunella vulgaris, Psychotria serpens,* and *Hyptis capitata*: Ursolic acid and related derivatives. *Planta Med.* 1988, 54, 308–11; Monks, A., Scudiero, D., Skehan, P., Shoemaker, R., Paull, K., Vistica, D., Hose, C., Langley, J., Cronise, P., Vaigro-Wolff, A., Gray-Goodrich, M., Campbell, H., Mayo, J., Boyd, M. Feasibility of a high-flux anticancer drug screen using a diverse panel of cultured human tumor cell lines. *J. Natl. Cancer Inst.* 1991, 83, 757–66; Paull, K. D., Shoemaker, R. H., Hodes, L., Monks, A., Scudiero, D. A., Rubinstein, L., Plowman, J., Boyd, M. R. Display and analysis of patterns of differential activity of drugs against human tumor cell lines: development of mean graph and COMPARE algorithm. *J. Natl. Cancer. Inst.* 1989, 81, 1088–92.]

Measurements of Cell Growth Inhibition and Data Analysis.

The details of measuring cell growth inhibition are described elsewhere [Monks, A., Scudiero, D., Skehan, P., Shoemaker, R., Paull, K., Vistica, D., Hose, C., Langley, J., Cronise, P., Vaigro-Wolff, A., Gray-Goodrich, M., Campbell, H., Mayo, J., Boyd, M. Feasibility of a high-flux anticancer drug screen using a diverse panel of cultured human tumor cell lines. *J. Natl. Cancer Inst.* 1991, 83, 757–66; amori, T., Sato, S., Chikazawa, H., Kadota, T. Anti-tumor efficacy of paclitaxel against human lung cancer xenografts. *Jpn. J. Cancer Res.* 1997, 88, 1205–10.] Briefly, the cells were plated at proper density in 96-well plates in RPMI 1640 with 5% fetal bovine serum and allowed to attach overnight. The cells were exposed to drugs for 48 h. Then, the cell growth was determined according to the Sulforhodamine B assay, described by Skehan et al [Skehan, P., Storeng, R., Scudiero, D., Monks, A., McMahon, D., Vistica, D., Warren, J. T., Bokesch, H., Kenney, S., Boyd, M. R. New calorimetric cytotoxicity assay for anticancer-drug screening. *J. Natl. Cancer Inst.* 1990, 82, 1107–12.] Data calculations were made according to the method described previously [Monks, A., Scudiero, D., Skehan, P., Shoemaker, R., Paull, K., Vistica, D., Hose, C., Langley, J., Cronise, P., Vaigro-Wolff, A., Gray-Goodrich, M., Campbell, H., Mayo, J., Boyd, M. Feasibility of a high-flux anticancer drug screen using a diverse panel of cultured human tumor cell lines. *J. Natl. Cancer Inst.* 1991, 83, 757–66.] Absorbance for the control well (C) and the tests well (T) were measured at 525 nm. Moreover, at time 0 (addition of drugs), absorbance for the test well ($T_0$) was also measured. Using these measurements, cell growth inhibition (percentage of growth) by each concentration of drug was calculated as: % growth=$100\times[(T-T_0)/(C-T_0)]$, when $T>T_0$ and 50% growth inhibition parameter ($GI_{50}$) was determined. The $GI_{50}$ was calculated as $100\times[(T-T_0)/(C-T_0)]=50$.

Results

Preliminary Screening of Antitumor Activity

Preliminary screening of antitumor activity was based on the cytotoxicity tested in human long cancer (A-549) cell lines. As shown in Table 1, 3-ethoxycarbonyl derivatives of substituted 2-phenyl-4-quinolones (VII-5, VII-7~10) did not show any significant activity. Among 3-carboxylic acid derivatives (IX), the cytotoxicity was not remarkable when the m-position of 2-phenyl group was substituted by $OCH_3$ group (IX-3, 7, 11). $ED_{50}$ values were greater than 20 μg/mL. On the contrary, the cytotoxicity increased greatly when the m-position was substituted by F atom (IX-2, 5, 8), 3'-fluoro-6-methoxy-2-phenyl-4-quinolone-3-carboxylic acid (IX-8) was the most potent compound with an $ED_{50}$ of 0.19 μg/mL. The replacement of F atom with Cl atom on the m-position (IX-1, 6, 9) caused the activity to decrease, which nevertheless were more active then the m-methoxy derivatives (IX-3, 7, 10). The antitumor activity was not good, if there was no substitution on the m-position of 2-phenyl group (IX-11).

TABLE 1

The cytotoxicity of ethyl 3',6-disubstituted 2-phenyl-4-quinolone-3-carboxylates (VII-5, VII-7~10, IX-1~3, IX-5~11) against lung cancer cell line (A-549).

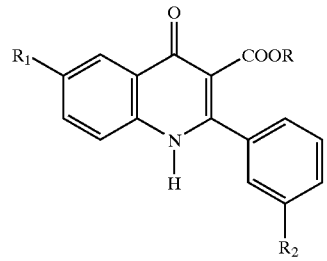

| Compound | R | $R_1$ | $R_2$ | $ED_{50}$ (μg/mL)[a] |
|---|---|---|---|---|
| VII-5 | $CH_2CH_3$ | Cl | F | >20 |
| VII-7 | $CH_2CH_3$ | Cl | $OCH_3$ | >20 |
| VII-8 | $CH_2CH_3$ | $OCH_3$ | F | NA |
| VII-9 | $CH_2CH_3$ | $OCH_3$ | Cl | >20 |
| VII-10 | $CH_2CH_3$ | $OCH_3$ | $OCH_3$ | >20 |
| IX-1 | H | F | Cl | 20 |
| IX-2 | H | F | F | 0.5 |
| IX-3 | H | F | $OCH_3$ | >20 |
| IX-5 | H | Cl | F | 1.80 |
| IX-6 | H | Cl | Cl | >20 |
| IX-7 | H | Cl | $OCH_3$ | >20 |
| IX-8 | H | $OCH_3$ | F | 0.19 |
| IX-9 | H | $OCH_3$ | Cl | 20 |
| IX-10 | H | $OCH_3$ | $OCH_3$ | >20 |
| IX-11 | H | $OCH_3$ | H | >20 |

[a]Cytotoxicity expressed as $ED_{50}$ against A-549 (the concentration of compounds that causes a 50% reduction in absorbance at 562 nm relative to untreated cells using the SRB assay) [Rubinstein, L. V.; Shoemaker, R. H.; Paull, K. D; Simo, R. M; Toshini, S; Skehan, P.; Scudiero, P. A.; Monks, A.; Boyd, M. R. Comparison of in vitro anticancer-drug-screening data generated with a tetrazolium assay versus a protein assay against a diverse panel of human tumor cell lines.*J. Natl. Cancer Inst.* 1990, 82, 1113-8].

The cytotoxicity of the tromethamine salts of compounds IX was presented in Table 2, the SARs were similar to the carboxylic acids (IX), namely, 3'-fluoro-derivatives (X-2, 5, 8) had the best activity followed by 3'-chloro-derivatives (X-1, 6, 9), and 3'-methoxy derivatives (X-3, 7, 10) had the weakest activity. Among these salts, the corresponding salt (X-8) of compound IX-8 again showed the best antitumor activity with an $ED_{50}$ of 2.4 μg/mL.

The SARs of the described above compounds IX and X revealed that the size of the substituents on the m-position of 2-phenyl group affected its activity greatly. We conjectured that the coplanarity between 2-phenyl group and quinolone ring had a strong influence in the activity. Meanwhile the results from preliminary screening indicated that compound IX-8 and X-8 had the best cytotoxicity against A-549. These two compounds were further tested on other 8 human tumor cell lines (HTCL) to evaluate their activities on the replication of these cell lines.

TABLE 2

The Cytotoxicity of ethyl 3',6-disubstituted 2-phenyl-4-quinolone-3-carboxylic acid tromethamine salts (X-1~3, X-4~11) against lung cancer cell line (A-549).

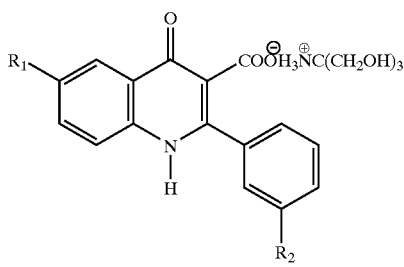

| Compound | $R_1$ | $R_2$ | $ED_{50}$ ($\mu$g/mL)[a] |
|---|---|---|---|
| X-1 | F | Cl | 17.6 |
| X-2 | F | F | 4.3 |
| X-3 | F | $OCH_3$ | NA |
| X-5 | Cl | F | 10.9 |
| X-6 | Cl | Cl | >20 |
| X-7 | Cl | $OCH_3$ | >20 |
| X-8 | $OCH_3$ | F | 2.4 |
| X-9 | $OCH_3$ | Cl | 17.6 |
| X-10 | $OCH_3$ | $OCH_3$ | NA |
| X-11 | $OCH_3$ | H | >20 |

[a]Cytotoxicity expressed as $ED_{50}$ against A-549 (the concentration of compounds that causes a 50% reduction in adsorbance at 562 nm relative to untreated cells using the SRB assay).

The Activity of Compounds IX-8 and X-8 Against HTLC Replication

Antitumor activity of compounds IX-8 and X-8 was further tested on the following 8 cancer cell lines: CAKI, HOS, KB, KB-VIN, SK-MEL-2, U87-MG, HCT-8 and IA9. As shown in Table 3, these two compounds demonstrated marked inhibition against almost all of these 8 cancer cell lines. It is worth mentioning that these two compounds were quite active against human ovarian cancer cells (IA9), which were known to have a high level of drug resistant P-glycoprotein. $IC_{50}$ of compound IX-8 against these cancer cells is only 0.03 $\mu$g/mL. Thus, this compound is really worth developing, particular against drug resistant ovarian cancer.

On the other hand, compound IX-8 was equally active against vincristine sensitive and resistant KB cells. It is also worth developing, against vincristine-resistant epidermal carcinoma of the nasopharynx.

Evaluation of Compound IX-8 Against Human Cancer Cell Line Panel

Our previous screening of cytotoxicity indicated that compound IX-8 possessed excellent antitumor activity. It was further evaluated against human caner cell line panel which includes 5 breast cancer, 6 CNS cancer, 5 colon cancer, 7 lung cancer, 1 melanoma, 5 ovarian cancer, 2 renal cancer, 6 stomach cancer, and 2 prostate cancer cell lines. These various cancer cells were cultured in 96 wells plate. Compound IX-8 was employed at 5 different dosages between $10^{-4}$ and $10^{-8}$ M, and cultured with the cells for 48 hr. Cells were stained with Sulforhodamine B for the assay of cell number. Dose response curves were obtained from computer analysis. $GI_{50}$ was obtained from such curves.

Compound IX-8 was active against most cancer cell lines. The MG-MID (mean growth midpoint) of log $GI_{50}$ is −6.22M. It was most effective against HGC2998 and the log $GI_{50}$ is −6.86M; next came against OVCAR-4 with a log $GI_{50}$ of −6.76 M.

TABLE 3

The activity of compounds IX-8 and X-8 against HTCL replication
$ED_{50}$ ($\mu$g/mL)[a]

| Compound | CAKI[b] | HOS[b] | KB[b] | KB-VIN[b] | SK-MEL-2[b] | U87-MG[b] | HCT-8[b] | IA9[b] |
|---|---|---|---|---|---|---|---|---|
| IX-8 | 10.0 | 0.14 | 0.13 | 0.13 | 0.16 | 1.50 | 0.14 | 0.03 |
| X-8 | NT | 5.0 | NT | NT | 2.0 | 5.0 | 1.20 | 0.88 |

[a]Cell line/mean $ED_{5g}$ in mcg/mL. (Huplieated varied no more than 5%)

Note:

if inhibition is less than 50% at 10 mcg/mL then inhibition values observed are the bracketed values.

NT = Not tested

[b]Renal cancer (CAKI), bone (HOS), epidermoid carcinoma of the nasopharynx (KB), Vincristine-resBtant epidermoid carcinoma of the nasopharynx (KB-VIN), melanoma (SK-MEL-2), glioblastoma (C187-MG), ileocecal Carcinoma (HCT-8) and human ovarian cancer (IA9) cell lines.

What is claimed is:

1. A substituted 2-phenyl-4-quinolone-3-carboxylic acid compound having the formula (i):

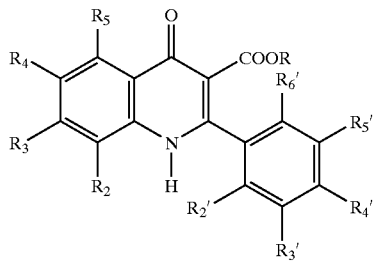

wherein $R_2'$, $R_3'$, $R_4'$, $R_5'$ and $R_6'$ independently are H, $(CH_2)_nCH_3$, $(CH_2)_nYH$, $Y(CH_2)_nCH_3$, $Y(CH_2)_nYH$, $Y(CH_2)_nNR_8R_9$, X, or $NR_8R_9$, wherein n is an integer of 0~4, Y is O or S, X is F, Cl, or Br, and $R_8$ and $R_9$ independently are H, $(CH_2)_nYH$, $(CH_2)_nN(C_nH_{2n+1})(C_mH_{2m+1})$ or $(CH_2)_nCH_3$, wherein n and Y are defined as above, and m is an integer of 0~4;

$R_2$, $R_3$, $R_4$ and $R_5$ independently are H, $(CH_2)_nCH_3$, $(CH_2)_nYH$, $Y(CH_2)_nCH_3$, $Y(CH_2)_nYH$, $Y(CH_2)_nNR_8R_9$, X, $NR_8R_9$,

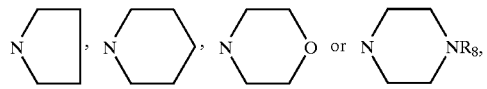

or $R_3$ and $R_4$ together is —$Y(CH_2)_nY$—, wherein n, Y, X, $R_8$ and $R_9$ are defined as above; and R is H provided that $R_3$ is not H.

2. The substituted 2-phenyl-4-quinolone-3-carboxylic acid compound according to claim 1, wherein $R_2'$, $R_4'$, $R_5'$ and $R_6'$ are H; and $R_3'$ is H, $Y(CH_2)_nCH_3$, $NH(CH_2)_nCH_3$ or X, wherein n, Y and X are defined as in claim 1; $R_3$ and $R_4$ is $Y(CH_2)_nCH_3$, or X, wherein n, Y and X are defined as in claim 1.

3. The substituted 2-phenyl-4-quinolone-3-carboxylic acid compound according to claim 2, wherein $R_3'$, and $R_4$ independently are methoxy, F or Cl.

4. The substituted 2-phenyl-4-quinolone-3-carboxylic acid compound according to claim 3, wherein $R_3'$ is F and $R_4$ is methoxy.

5. The substituted 2-phenyl-4-quinolone-3-carboxylic acid compound according to claim 2, wherein $R_3$ and $R_4$ together is —$OCH_2O$—.

6. A salt of a substituted 2-phenyl-4-quinolone-3-carboxylic acid compound of the formula (I) as set forth in any one of claim 1 to claim 5.

7. The salt according to claim 6, which is a quaternary ammonium salt.

8. The salt according to claim 6, which is a pharmaceutically acceptable inorganic salt.

9. A pharmaceutical composition for the killing of solid tumor cells, which comprises a therapeutically effective amount of a substituted 2-phenyl-4-quinolone-3-carboxylic acid compound of the formula (I) as set forth in any one of claim 1 to claim 5 or a pharmaceutically acceptable salt thereof, as an active ingredient, in admixture with a pharmaceutically acceptable carrier or diluent for the active ingredient, wherein the solid tumor cells comprise human breast cancer, CNS cancer, colon cancer, lung cancer, melanoma, ovarian cancer, renal cancer, stomach cancer, prostate cancer, ileocecal carcinoma, glioblastoma, bone cancer, or epidermoid carcinoma of the nasopharynx.

10. A substituted 2-phenyl-4-quinolone-3-carboxylic acid compound having the formula (i):

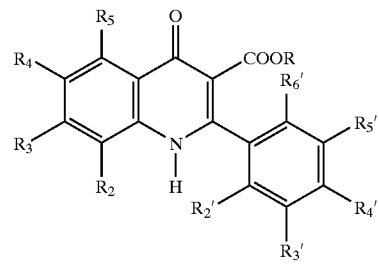

wherein $R_2'$, $R_4'$, $R_5'$ and $R_6'$ are H; and $R_3'$ is H, $Y(CH_2)_nCH_3$, $NH(CH_2)_nCH_3$ or X; $R_3$ is H; and $R_4$ is $Y(CH_2)_nCH_3$, or X; wherein n is an integer of 0~4; Y is O or S; X is F, Cl, or Br;

$R_2$, and $R_5$ independently are H, $(CH_2)_nCH_3$, $(CH_2)_nYH$, $Y(CH_2)_nCH_3$, $Y(CH_2)_nYH$, $Y(CH_2)_nNR_8R_9$, X, $NR_8R_9$,

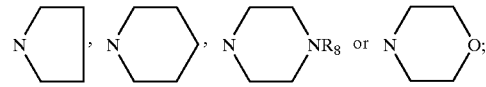

wherein n, Y, X, are as defined above and $R_8$ and $R_9$ independently are H, $(CH_2)_nYH$, $(CH_2)_nN(C_nH_{2n+1})(C_mH_{2m+1})$ or $(CH_2)_nCH_3$, wherein n and Y are defined as above, and m is an integer of 0~4; and R is H.

11. The substituted 2-phenyl-4-quinolone-3-carboxylic acid compound according to claim 10, wherein $R_3'$, and $R_4$ independently are methoxy, F or Cl.

12. The substituted 2-phenyl-4-quinolone-3-carboxylic acid compound according to claim 11, wherein $R_3'$ is F and $R_4$ is methoxy.

13. The substituted 2-phenyl-4-quinolone-3-carboxylic acid compound according to claim 11, wherein $R_3$ and $R_4$ together is —$OCH_2O$—.

* * * * *